US010632222B2

(12) United States Patent
Kelsen

(10) Patent No.: US 10,632,222 B2
(45) Date of Patent: Apr. 28, 2020

(54) DIGITAL AROMA DISPERSION SYSTEM AND DEVICES

(71) Applicant: Inhalio, Inc., Scotts Valley, CA (US)

(72) Inventor: Keith Kelsen, Scotts Valley, CA (US)

(73) Assignee: INHALIO, INC., Scotts Valley, CA (US)

(*) Notice: Subject to any disclaimer, the term of this patent is extended or adjusted under 35 U.S.C. 154(b) by 240 days.

(21) Appl. No.: 15/747,092

(22) PCT Filed: Sep. 22, 2016

(86) PCT No.: PCT/US2016/053090
§ 371 (c)(1),
(2) Date: Jan. 23, 2018

(87) PCT Pub. No.: WO2017/053553
PCT Pub. Date: Mar. 30, 2017

(65) Prior Publication Data
US 2018/0369442 A1 Dec. 27, 2018

Related U.S. Application Data

(60) Provisional application No. 62/221,650, filed on Sep. 22, 2015.

(51) Int. Cl.
| A61L 9/14 | (2006.01) |
| A61L 9/12 | (2006.01) |
| A61L 9/04 | (2006.01) |
| H04W 4/38 | (2018.01) |
| G06F 3/16 | (2006.01) |
| G06K 7/10 | (2006.01) |

(52) U.S. Cl.
CPC .................. *A61L 9/14* (2013.01); *A61L 9/04* (2013.01); *A61L 9/12* (2013.01); *A61L 9/122* (2013.01); *G06F 3/167* (2013.01); *G06K 7/10297* (2013.01); *H04W 4/38* (2018.02); *A61L 2209/111* (2013.01); *A61L 2209/133* (2013.01); *A61L 2209/16* (2013.01)

(58) Field of Classification Search
CPC ..... A61L 9/04; A61L 9/12; A61L 9/14; A61L 9/122; A61L 2209/111; A61L 2209/133; A61L 2209/16; G06F 3/167; G06K 7/10297; H04W 4/38
USPC .............................. 261/30, DIG. 88, DIG. 89
See application file for complete search history.

(56) References Cited

U.S. PATENT DOCUMENTS 6,371,451 B1 * 4/2002 Choi ................. A45D 34/02
261/115
6,783,117 B2 * 8/2004 Wohrle ................. A61L 9/035
261/104

(Continued)

*Primary Examiner* — Charles S Bushey
(74) *Attorney, Agent, or Firm* — Staniford Tomita LLP

(57) ABSTRACT

The present invention is directed to a digital aroma system that provides a scented air on demand to various devices in various forms and user held devices including: remote controls and mobile computing devices. Dry fragrance infused substrates are contained in fragrance cartridges that are removably mounted in a cassette that is connected to a manifold that has airway passages that are connected to fans or pumps that are controlled by a computer processor. In response to a fragrance control signal, the processor can selectively direct scented air having a specified fragrance to a system user.

22 Claims, 19 Drawing Sheets

(56) References Cited

U.S. PATENT DOCUMENTS

| | | | | |
|---|---|---|---|---|
| 7,484,716 B2* | 2/2009 | Ford Morie | ............ | G06F 3/011 |
| | | | | 261/26 |
| 9,364,575 B2* | 6/2016 | Habbel | .................. | A61L 9/122 |
| 10,058,627 B2* | 8/2018 | Kelsen | .................... | A63F 13/24 |
| 2018/0169288 A1* | 6/2018 | Kelsen | .................... | A61L 9/122 |

* cited by examiner

DIGITAL AROMA DISPERSION SYSTEM AND DEVICES

CROSS REFERENCE TO RELATED APPLICATIONS

This patent application claims priority to U.S. Provisional Patent Application No. 62/221,650, "Digital Aroma Cassette Cartridge and Dispersion System Connected Home Devices," filed Sep. 22, 2015, which is hereby incorporated by reference in its entirety.

FIELD OF INVENTION

This invention relates to aroma devices and systems for creating an aroma and smell experience where individuals interact with a device connected to a network that can be remotely controlled through a computing device. In response to control signals from the computing device, the aroma device can deliver a dry fragrance into a space.

BACKGROUND

Fragrance systems exist for commercial and home applications. In some embodiments, fragrance systems provide aromas, which can elicit various emotional feelings that can improve moods and increase feelings of happiness. Devices exist which distribute fragrances for commercial and home applications. For example, scented oils have been used to emit fragrances. However, many scented oils such as pine oil, lavender oil, geranium oil, etc. include monoterpenes, which may be carcinogenic. Some studies have shown that rats and mice that had scented oils injected into their throats, resulted in kidney tumors. What is needed is an improved fragrance system that can be portable to deliver fragrances to home spaces that does not use scented oils and is not carcinogenic.

SUMMARY OF THE INVENTION

The present invention is directed to a digital aroma system that provides aroma experiences that can be utilized by consumers via dry fragrance infused beads or other solid substrates that contain porous fragrance materials within a fragrance cartridge(s). The fragrance cartridges can be removable and mounted in an interchangeable cassette system that connects to a manifold within an aroma device. The manifold has specific airway passages that are connected to fans or pumps that are controlled by a computer processor. In response to a fragrance control signal, the processor can selectively actuate fans or air pumps to direct air into the user selected target fragrance cartridge. More specifically, the processor causes the fan or pump to pull or push fresh unscented air through the target fragrance cartridge so that the fresh air passes by the particles infused with a dry fragrance material. The aroma reaches the individual through one or several outlets.

The digital aroma system is an invention designed to output many different aromas into an area such as a room of a house and is controlled or programed by the user. In an embodiment, the digital aroma system can simultaneously hold numerous (for example six) distinct fragrance cartridges. The digital aroma system can communicate with user devices such as a remote control or a computing device such as a smart phone, tablet computer or other computer; it can include several components that can communicate with radio frequency (RF) signals that can be transmitted directly between the aroma device and the controller (remote control or computing device). In other embodiments, the system can communicate with a network such as the internet.

The digital aroma system invention can include a processor and a controller that runs computer software to creates a smell sensory experience. This computer processor of the digital aroma system can also communicate with remote computers in a cloud based system and/or a remote server. These remote computers can interact with the local digital aroma system software to provide live interactive experiences to the system users. In an embodiment, the digital aroma system can communicate wirelessly through Blue Tooth, Wi-Fi, RFID or similar technologies with other devices which can provide control signals for releasing fragrances.

The digital aroma system can include a processor that can control and monitor the operation of the system components. The processor can be coupled to fans and/or valves to selectively direct air to the target fragrance cartridge. When a desired wireless fragrance signal is received, the processor can interpret the fragrance signal and direct fresh air through the air inlet to the target fragrance cartridge. The dry fragrance can mix with the fresh air and be directed to a scent outlet to the system user. In some embodiments, the processor can direct fresh air through two or more target fragrance cartridges to provide a mixed fragrance to the user. The scent is provided as a limited predetermined period of time or volume of air. Once the scent is provided to the user, the processor can stop the flow of air through the fragrance cartridge by stopping a fan(s) or closing a valve(s). In an embodiment, the processor can be programmed to flush the scent outlet of the manifold periodically with fresh air so that subsequent fragrances are not mixed or contaminated. For example, the processor may direct fresh air through the scent outlet after each fragrance output by the system.

The digital aroma system can release fragrances based upon fragrance signals. The digital aroma device can include a receiver, which receives fragrance signals. In response to the fragrance signals, the processor can identify the corresponding target fragrance cartridge and direct air to the target fragrance cartridge, which can result in the dry fragrance device delivering a dry fragrance aroma to the user. The fragrance cartridges can have a specific number of dispersions and the system can inform the user when the individual fragrance cartridges need to be replaced.

BRIEF DESCRIPTION OF THE DRAWINGS

The present invention will be readily understood by the following detailed description in conjunction with the accompanying drawings, wherein like reference numerals designate like structural elements, and in which:

FIG. 2 illustrates a bottom perspective view of an embodiment of a fragrance cartridge.

FIG. 3 illustrates a side view of an embodiment of a fragrance cartridge.

FIG. 4 illustrates a bottom perspective view of an embodiment of a fragrance cartridge.

FIG. 5 illustrates a top view of an embodiment of a cassette that holds a plurality of fragrance cartridges.

FIG. 6 illustrates a top perspective view of an embodiment of a cassette.

FIG. 7 illustrates a side view of an embodiment of a cassette.

FIG. 8 illustrates a top perspective view of an embodiment of a cassette with a plurality of fragrance cartridges.

FIG. 9 illustrates a perspective view of an embodiment of a cassette with a plurality of fragrance cartridges.

FIG. 10 illustrates a top perspective view of an embodiment of a cassette with a plurality of fragrance cartridges.

FIG. 11 illustrates a top view of an embodiment of a controller with a digital aroma system.

FIG. 12 illustrates a bottom view of an embodiment of a controller with a digital aroma system.

DETAILED DESCRIPTION

A detailed description of one or more embodiments of the invention is provided below along with accompanying figures that illustrate the principles of the invention. While the invention is described in conjunction with such embodiment(s), it should be understood that the invention is not limited to any one embodiment. On the contrary, the scope of the invention is limited only by the claims and the invention encompasses numerous alternatives, modifications, and equivalents. For the purpose of example, numerous specific details are set forth in the following description in order to provide a thorough understanding of the present invention. These details are provided for the purpose of example, and the present invention may be practiced according to the claims without some or all of these specific details. For the purpose of clarity, technical material that is known in the technical fields related to the invention has not been described in detail so that the present invention is not unnecessarily obscured.

Figure 1:
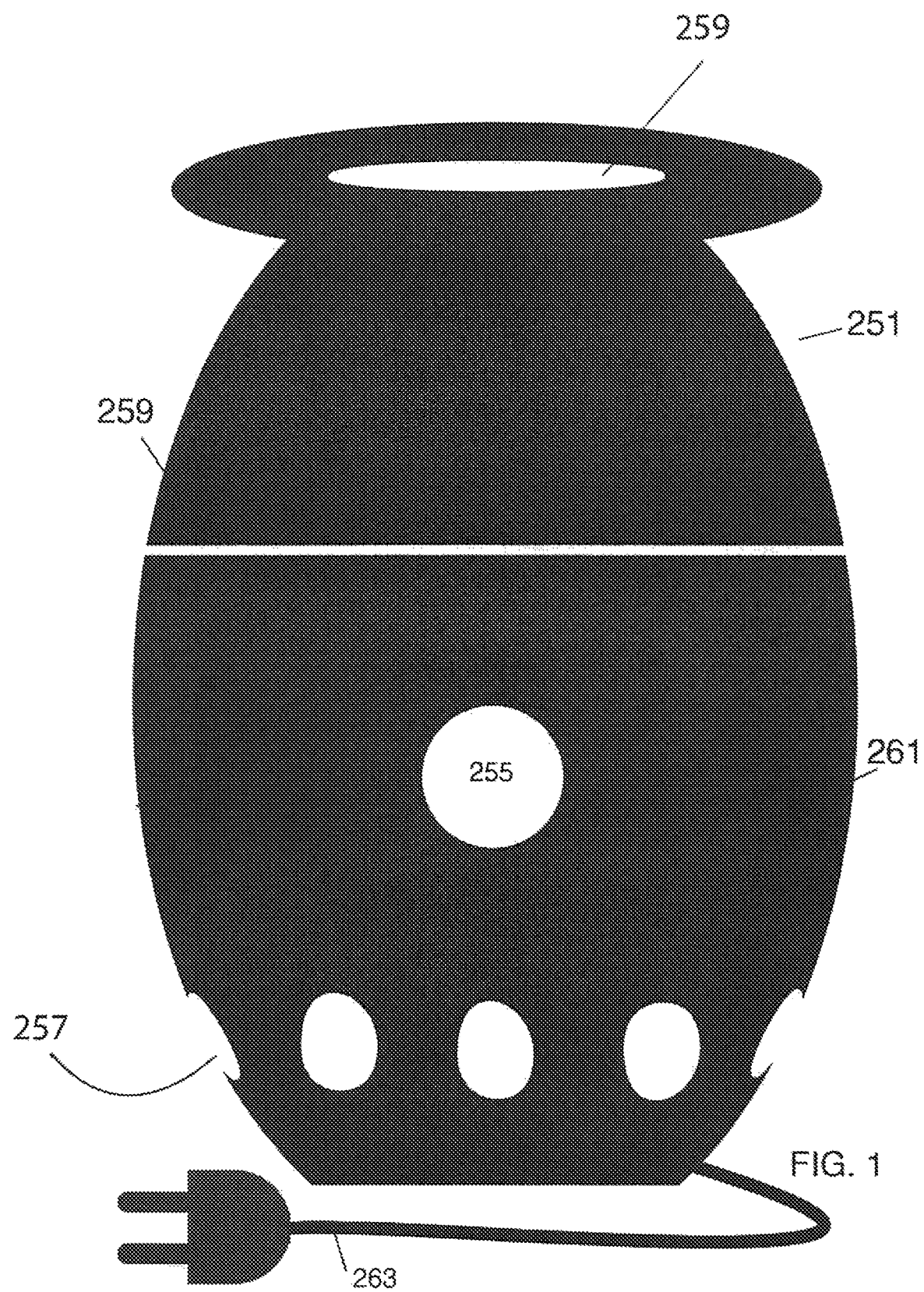
FIG. 1 illustrates a side view of an embodiment of an aroma device.
Figure 2:
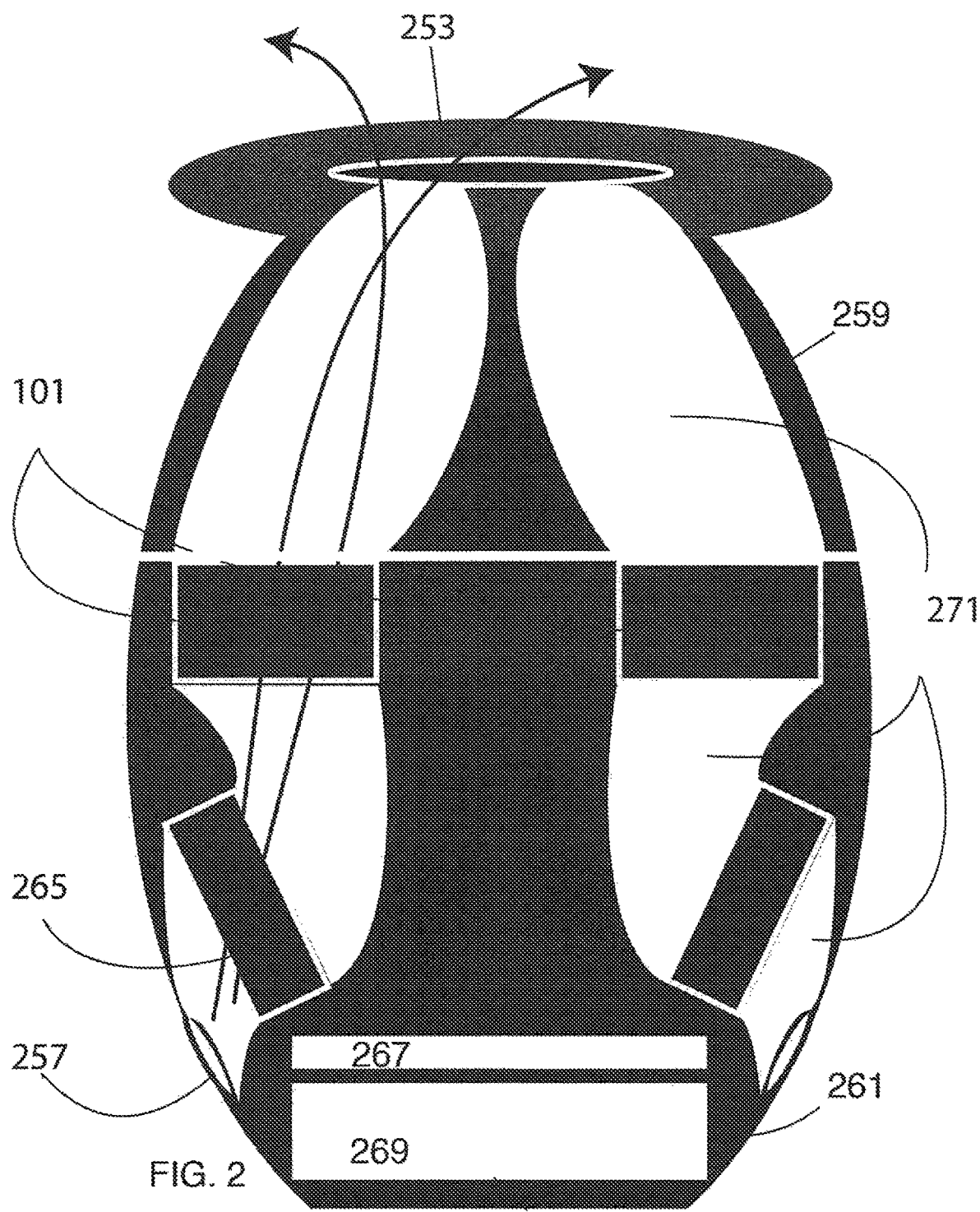
FIG. 2 illustrates a cross section side view of an embodiment of an aroma device.

FIG. 1 illustrates a side view and FIG. 2 illustrates a cross section view of a vase shaped portable aroma unit 251 that includes fresh air inlets 257, scented air outlets 253, fragrance cartridges 101 containing different dry particle fragrances, fans 265, a controller 267. The aroma unit 251 can have a plurality of air channels 271 which provide separate air flow paths for each of the fragrance cartridges. Air traveling through one air channel 271 does not become mixed with air traveling through another air channel 271. In an embodiment, each of the air channels 271 can have a dedicated fan 265, fragrance cartridge 101 and air inlet 257. In an embodiment, the aroma unit 251 can have an upper portion 259 and a lower portion 261 which can be separated to access the internal components. For example, the upper portion 259 can be detached from the lower portion 261 to access and replace the fragrance cartridges 101.

The controller 267 and power supply 269 can be located in a lower portion of the portable aroma unit 261 possibly below the fans 265 so that the upper portion 259 does not include any electrical components. The fans 265 and controller 267 can be powered by an electrical power supply 269, which can be a battery coupled to a power cord 263 that can be coupled to a power source such as an AC outlet. The battery can be charged by the external power source, which can also power the fans 265 and controller 267. When the aroma unit 251 is moved, the charged battery can be used to power the fans 265 and controller 267.

The controller 267 can include a central processing unit (CPU) and a radio frequency (RF) receiver and a computing device that can transmit a fragrance control signal to the aroma unit 251. The controller 267 can identify the desired fragrance from the fragrance control signal and in response to this signal actuate the controller 267 that can actuate the fan 265 corresponding to the desired fragrance. The actuated fan 265 can draw fresh air from the inlet 257 and direct the fresh air through the desired fragrance cartridge 101. Some of the dry fragrance particles from the desired fragrance cartridge 101 can mix with the fresh air and be emitted from the aroma unit 251 out of the outlet 253 and dispersed in a room or an area. The controller 267 can actuate the fan 265 for a predetermined period of time so that the desired fragrance flows around the vicinity of the aroma unit 251 but is not excessive. After the predetermined period of times expires, the controller 267 can turn off the fan 265 to stop the flow of fragrance particles out of the aroma unit 251. In another embodiment, the controller 267 can periodically turn the fan 265 on and off multiple times to maintain a fragrance in the area until instructions to discontinue the cycling of the fan 265 are received.

In an embodiment, the aroma unit 251 can include a visual display 255 such as an LCD or LED screen that is coupled to the controller 267 and configured to the display information about the aroma unit 251. For example, during a set up procedure, the display 255 can show the RF network connection status, which can be the Wi-Fi connection status. Once the aroma unit 251 is connected to the network, the visual display 255 can show the name of the scent it is diffusing to the outlet. When the aroma unit is not outputting a fragrance, the display 255 can output general information such as: time, day, date, etc.

In an embodiment, each fragrance cartridge can have a life that is represented by a specific predetermined number of air flows or a specific duration of air flow. The controller 267 can keep track of the air flows or a specific duration of air flow applied to each fragrance cartridge 101. When a fragrance cartridge is nearly depleted and needs to be replaced, the controller 267 can cause the visual display 255 to display the cartridge replacement information. A user can see this replacement information on the display 255 and replace the fragrance cartridge. If the fragrance cartridge 101 is not replaced, the controller can discontinue controlling the fan 265 for the expired fragrance cartridge. In an embodiment, the controller 267 can transmit notices by RF signals through an RF transmitter on the controller 267 to the user's computing device thus informing him or her that the fragrance cartridge(s) 101 need to be replaced.

With reference to FIG. 2, in an embodiment the vase shape aroma unit 251 can include fresh air inlets 257 at the bottom of the housing and an outlet 253 at a top of the housing. The aroma unit 251 can be placed on the floor or a structure such as a table within a room having a volume or space. The floor and table in a lower portion of the room space and the aroma units 251 can output the fragrances upward to evenly distribute the fragrances within the room. By drawing air in from a lower portion of the space and directing the scented air upward, the fragrance can be distributed throughout the entire volume of the room. When the fan 265 is actuated, air is sucked through the corresponding inlet 257 and directed up through the lower air channel 271 and then through the fan 265. The fan 265 pushes the air further up through the air channel and through the cartridge 101 which can be filled with beads or a polymer substrate. Dry fragrance particles can be removed from the beads or substrate and mix with the air. This scented air can then be directed through the upper air channel 271 and exit the outlet 253 at the top of the aroma unit 251.

Figure 3:
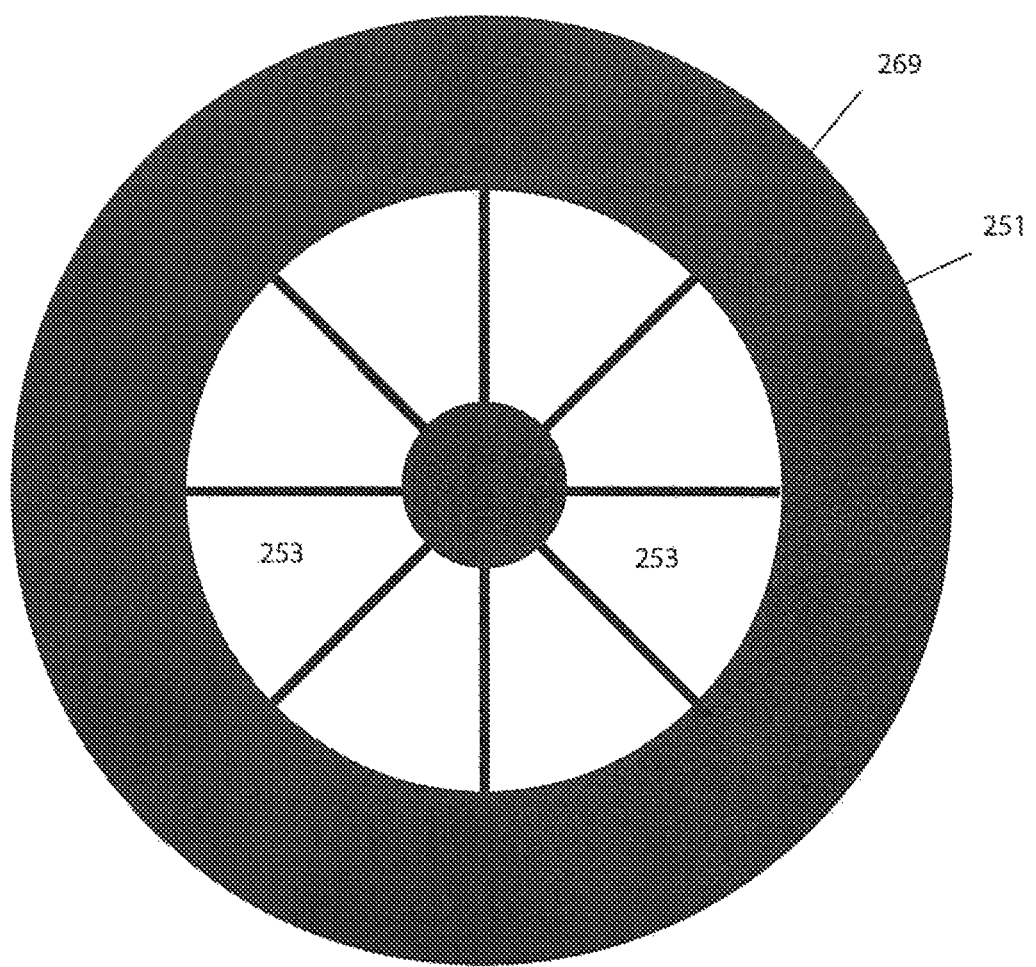
FIG. 3 illustrates a top view of an upper portion of an embodiment of an aroma device.
Figure 4:
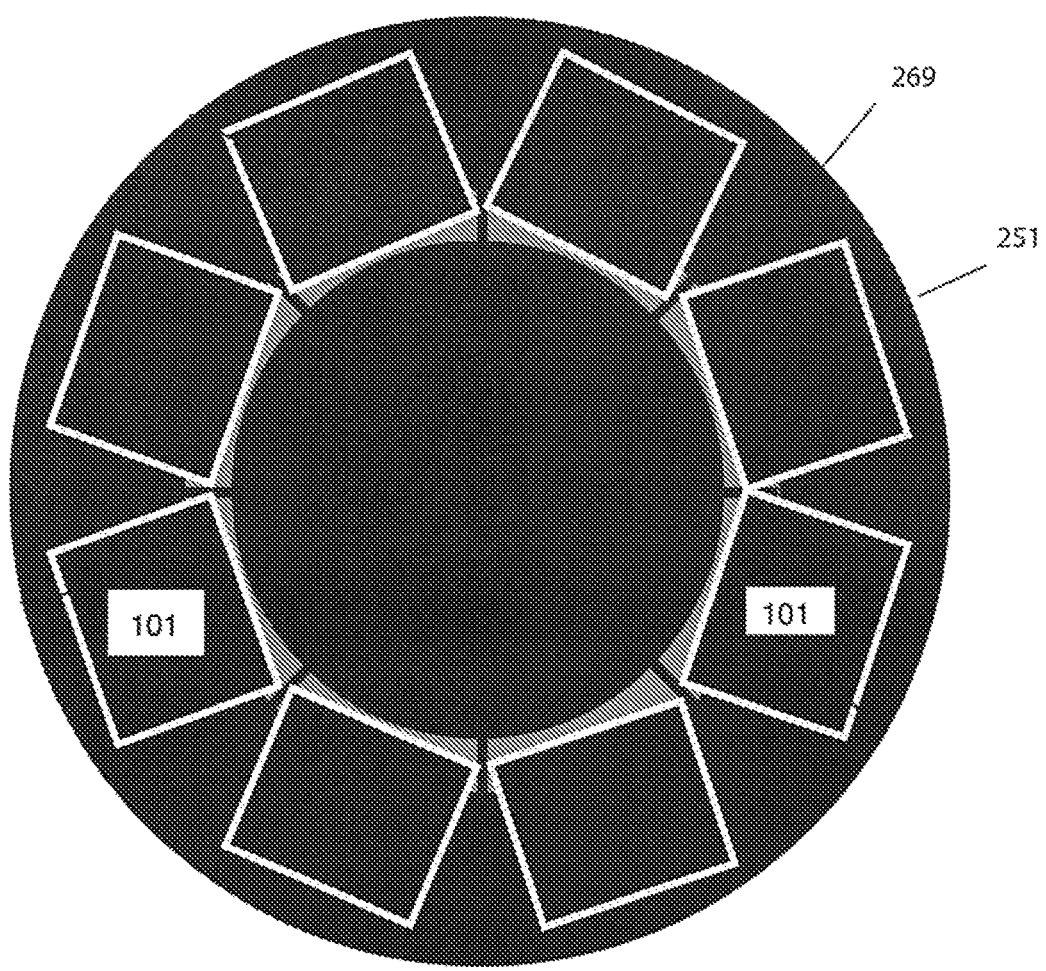
FIG. 4 illustrates a top view of a lower portion of an embodiment of an aroma device.

FIG. 3 illustrates a top view of an embodiment of the upper portion 269 of the aroma unit 251 and FIG. 4 illustrates a top view of a lower portion 261 of the aroma unit 251 when the upper portion 269 is removed. In this example, there are eight different fragrance cartridges 101 held in the lower portion 261 of the aroma unit 251. Each of the eight different fragrance cartridges 101 can have a dedicated and separate air flow channel and outlet 253. Each of the air show channels can occupy a different radial segment around the perimeter of the aroma unit 251. In this example, there are eight different outlets 253. In different embodiments, there can be any number of outlets 253 with the number of outlets matching the number of air flow channels and fragrance cartridges in the aroma unit 251. With reference to FIG. 4, when a fragrance cartridge 101 needs to be replaced, the user can remove the upper portion 269 to access the internal fragrance cartridges 101. The user can remove the depleted fragrance cartridge 101 and replace it with a fresh fragrance cartridge 101. In an embodiment, the cartridges 101 can have seals, which can keep the internal contents fresh. These seals can be removed from the fresh fragrance cartridge 101 before they are installed in the lower portion 261 of the aroma unit 251.

Figure 5:
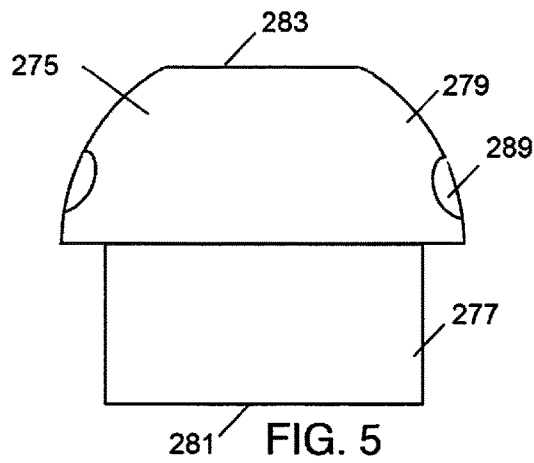
FIG. 5 illustrates a side view of an embodiment of a fragrance cartridge.
Figure 6:
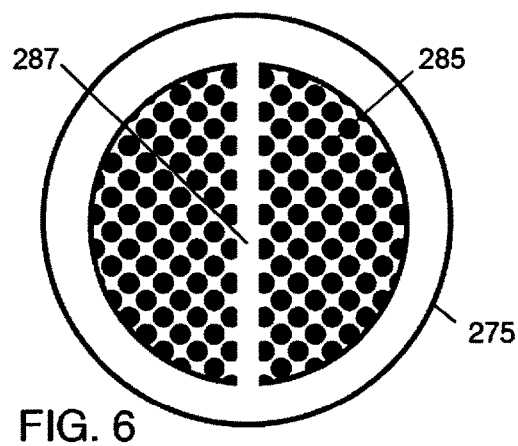
FIG. 6 illustrates a bottom view of an embodiment of a fragrance cartridge.
Figure 7:
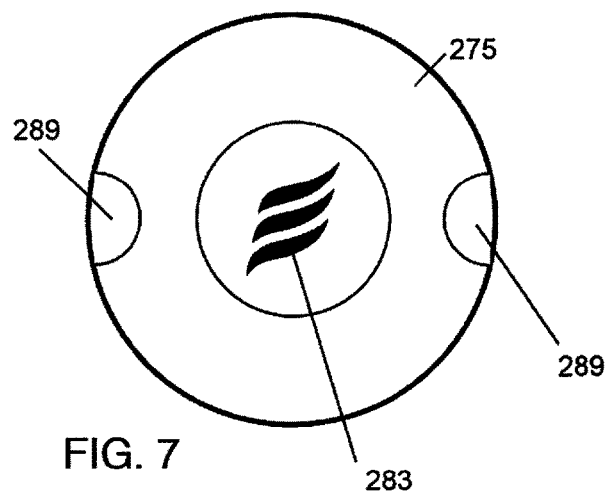
FIG. 7 illustrates a bottom view of an embodiment of a fragrance cartridge.

With reference to FIGS. 5-9 another embodiment of an individual aroma cartridge 275 is illustrated. FIG. 5 illustrates a side view, FIG. 6 illustrates a bottom view and FIG. 7 illustrates a top view of the aroma cartridge 275. In this embodiment, the lower portion 277 of the cartridge can have a cylindrical outer surface shape and the upper section 279 can have a hemispherical outer surface shape. This aroma cartridge 275 can include interchangeable housing designs that can be used in digital aroma cassette cartridge and matrix dispersion systems and other systems. As shown in FIG. 6, the bottom view of the aroma cartridge 275 shows a grated opening 285 that has holes that are smaller in diameter than the dry fragrance beads or substrates. The grated opening 285 allows air to pass through the cartridge 275. With reference to FIG. 7, the top view of the cartridge 275 shows the air vent outlet 283 for air flow out of the cartridge 275. The widths or openings of the air vent outlet 283 can be smaller than the diameters or widths of the dry fragrance beads or substrates. In an embodiment, the upper portion 279 can have thumb and index finger indents 289, which can be grasped so a user can twist the cartridge 275 to remove it from a cassette or a base.

Figure 8:
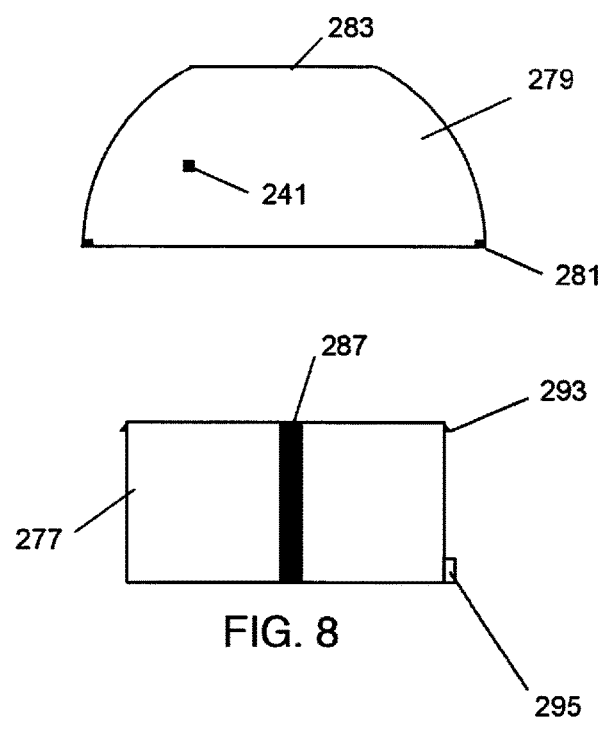
FIG. 8 illustrates a side exploded view of an embodiment of a fragrance cartridge.

With reference to FIG. 8, a cross section side view of the cartridge 275 is shown with the upper section 279 separated from the lower section 277. In an embodiment, the upper section 279 and the lower section 277 can snap fit together using a Ridge 291 on the upper section 279 that can lock to a tab 293 on the lower section 277. The ridge 291 can match the tab 293 which can be keyed to the ridge 291. The connection between the ridge 291 and the tab 293 can lock the upper section 279 and the lower section 277 together when assembled. The lower section 277 can also include a key 295 that protrudes outward from the cylindrical surface. The cartridge 275 can be placed in a corresponding opening in a cassette or base of an aroma unit. The key 295 can be aligned with a slot in the opening of the cassette or base when the cartridge is inserted. When the cartridge 275 is fully inserted, the user can rotate the cartridge 275 so that the key 295 is offset from the slot. This can lock the cartridge 275 in the cassette or base until the key 295 is rotated into alignment with the slot when it is removed for replacement as described above with reference to FIGS. 5-8.

Figure 9:
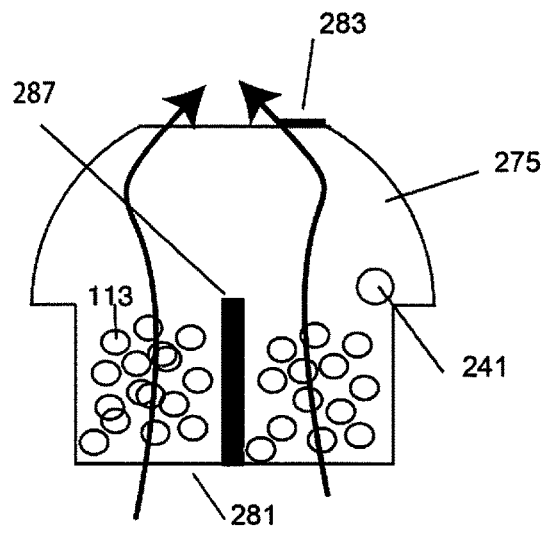
FIG. 9 illustrates a cross section side view of an embodiment of a fragrance cartridge.

FIG. 9 illustrates a cross section side view of a fragrance cartridge 275. Aroma beads or substrates 113 are placed within the cartridge 275. In the upright position, the substrates 113 rest on the grate 285 on both sides of the divider 287. Each cartridge 275 can be fitted with an RFID Tag 241 that provides RF data signals that identify the cartridge 275 matched to the system and the type of aroma in the cartridge 275. The RFID tag 241 can be read by an RFID reader which can transmit the RF data signals to the controller as described above.

Figure 10:
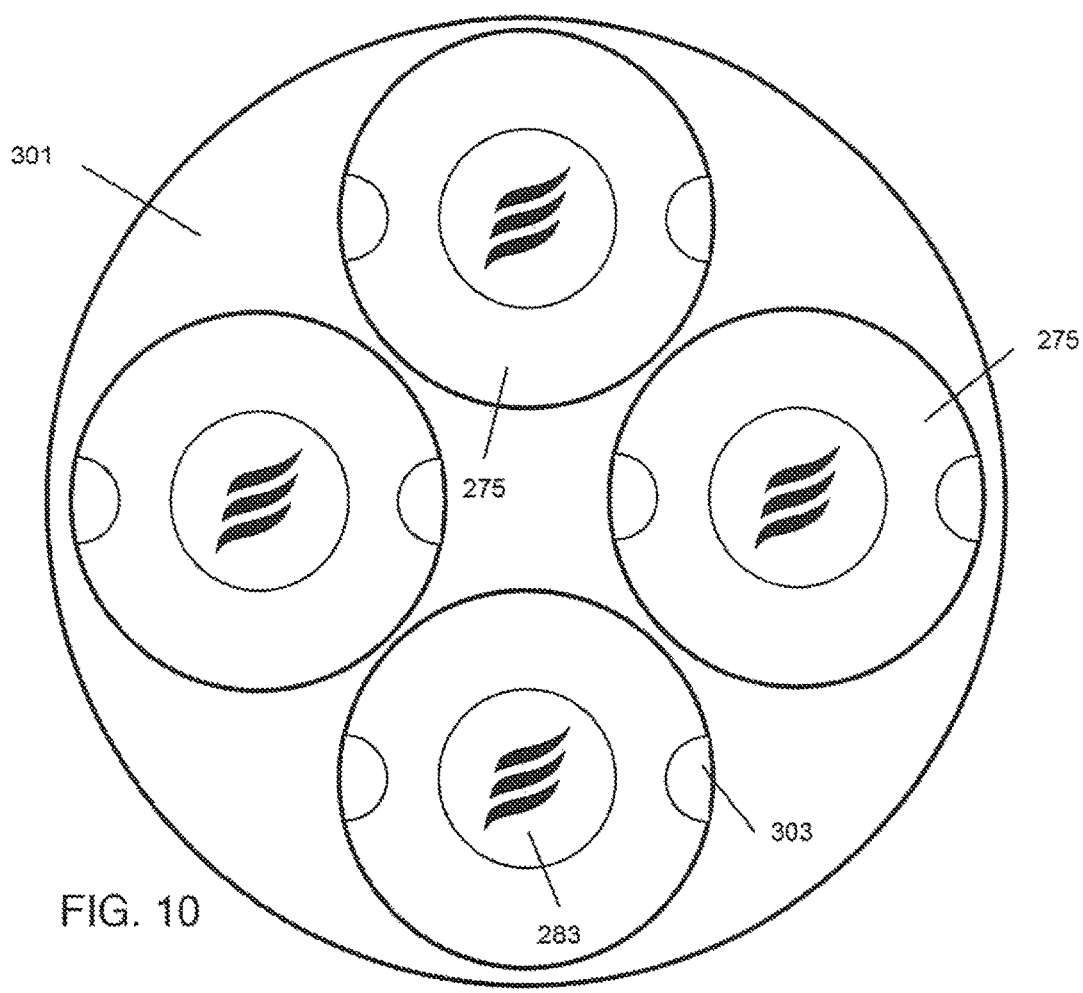
FIG. 10 illustrates a top view of an embodiment of an aroma device.
Figure 11:
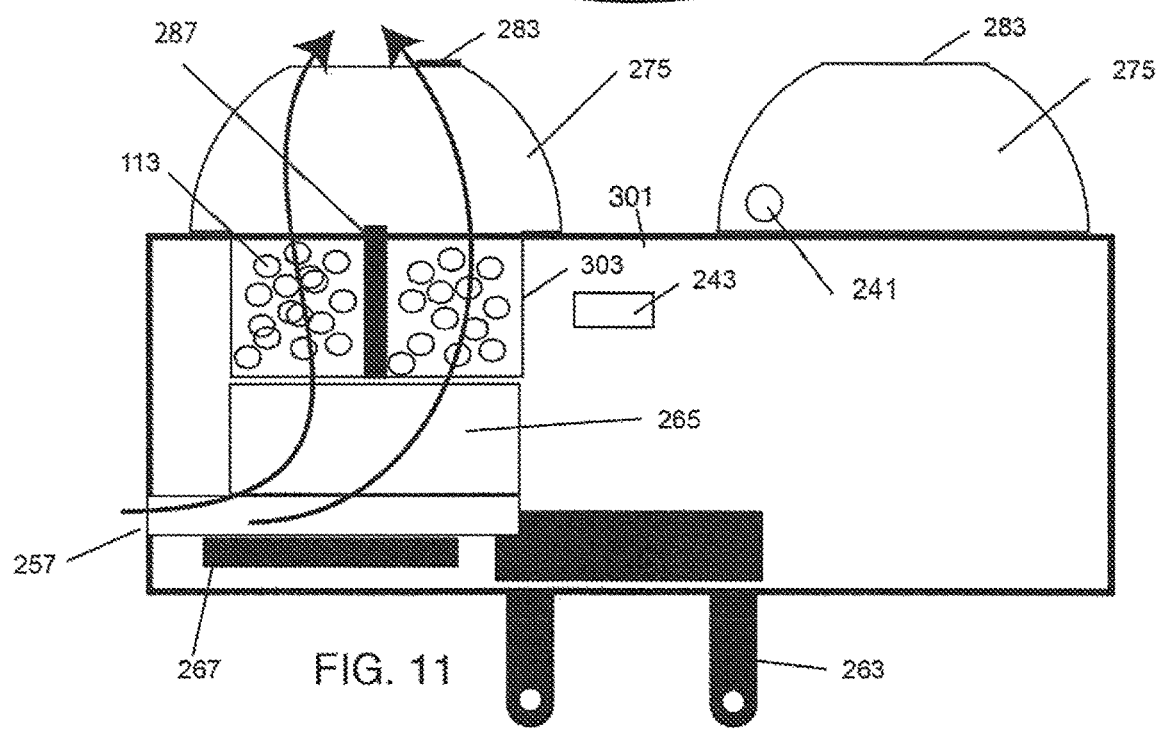
FIG. 11 illustrates a side cross section view of an embodiment of an aroma device.

With reference to the top view in FIG. 10 and with reference a cross section side view in FIG. 11, another embodiment of an aroma device 301 is illustrated. In this example, the aroma device 301 has a circular shape and cylindrical slots 303 for four fragrance cartridges 275. In this embodiment, the aroma device 301 is a base and together with the cartridges 275 this assembly forms another complete embodiment of the Digital Aroma Cassette Cartridge and Matrix Dispersion System.

FIG. 11 illustrates the internal components of the aroma device 301 and shows how the cartridge 275 sits in the slot 303 in the base of the aroma device 301. A fan 265 can be positioned directly under each of the cartridge slots 303 and a controller 267 and a power source 263 can also be mounted within the base of the aroma device 301. The controller 267 can include an RF receiver or transceiver and an RFID reader. In an embodiment, the aroma device can have a power source 263 which can include an integrated plug that can allow the base to be directly plugged into a wall outlet power source. Alternatively, the power source 263 can include a battery, which can be charged by the external power source or used independently to power the electrical components. When a cartridge 275 is placed in a slot 303, the RFID reader can read the RFID tag 241, which can include various cartridge information such as: fragrance, use number ratings, batch information for quality control, etc. The controller 267 can then store the fragrance data for actuation when a fragrance request signal is received. When the controller 267 receives a fragrance signal, it can respond by actuating the fan 265 associated with the desired fragrance from the fragrance request signal. The fan 265 pulls air in through a fresh air inlet 257 and then blows the fresh air through the fragrance cartridge 275 where dry fragrance particles mix with the air and exit the outlet 283. The upward directed scented air can then mix with the ambient air to disperse the fragrance. As discussed, the controller 267 can command the fan 265 to blow for a limited period of time and may repeat at regular intervals or on a timer as programmed by the user or as described above.

Figure 12:
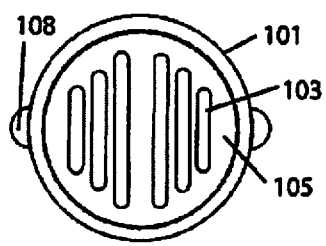
FIG. 12 illustrates a bottom view of an embodiment of a fragrance cartridge.
Figure 13:
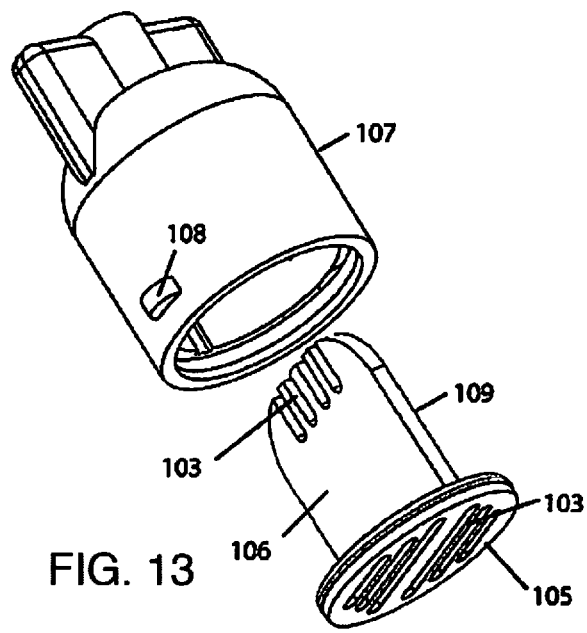
FIG. 13 illustrates the components of an embodiment of a digital aroma system.
Figure 14:
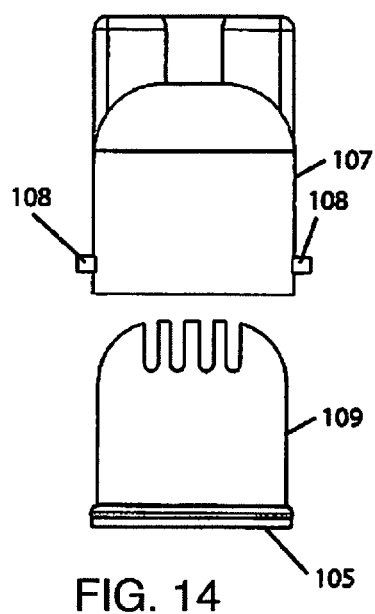
FIGS. 14 and 15 illustrate bottom views of different embodiments of controllers with the cassettes removed.
Figure 15:
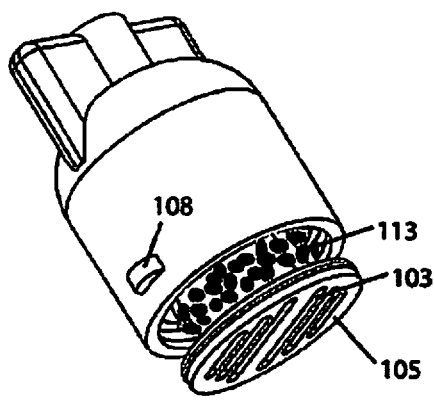

In other embodiments, different types of fragrance cartridges can be used with the aroma devices. In the illustrated examples, fresh air flows into a bottom of the fragrance cartridge and the scented air exits the top of the cartridge. An alternative embodiment of a fragrance cartridge is illustrated in FIGS. 12-15. In contrast to the fragrance cartridge illustrated in FIGS. 5-9 where the inlet and outlet are on opposite sides of the cartridge, in other embodiments, the air flow inlet and outlet can be on the same side of the fragrance cartridge. FIG. 12 illustrates a bottom view of an embodiment of the fragrance cartridge 101 with a plurality of air flow slots 103 in the bottom surface 105. FIG. 13 illustrates a perspective view of the fragrance cartridge 101 in a disassembled state. In this embodiment the fragrance cartridge 101 includes an upper housing 107 which has an internal volume and a lower housing 109 which has a lower surface 105 and a center divider 106 having air flow slots 103. FIG. 14 illustrates a side view of a fragrance cartridge 101 that has a two piece housing that includes an upper housing 107 and a lower housing 109 that are secured together to form the complete housing for the fragrance cartridge 101. FIG. 15 illustrates a perspective view of the fragrance cartridge 101 in a disassembled state. The upper housing 107 can be filled with a plurality of substrates 113 that are infused with a dry fragrance. In an embodiment the substrates 113 can be spherical balls or other three dimensional objects such as cubes, cylinders, particles or other geometric volumes. While the fragrance cartridge 101 is illustrated as a dome shape with slots 103 in the lower surface 105 and the lower housing 109, in other embodiments the fragrance cartridge can have any other geometric shape that can hold the plurality of substrates 113. When air flows through the cartridge 101, the dry fragrance can mix with the air and be removed from the substrates 113 resulting in scented air exiting the cartridge 101. In an embodiment, the fragrance cartridge 101 can have a cylindrical shape that can be placed into a corresponding cylindrical bore. In an embodiment tabs 108 can be mounted on the outer surface of the cartridge 101 which are used to secure the cartridge to a cassette.

Figure 16:
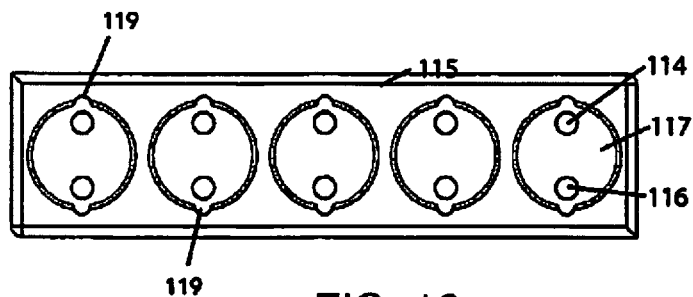
FIG. 16 illustrates an embodiment of a headset that includes an integrated digital aroma system.
Figure 17:
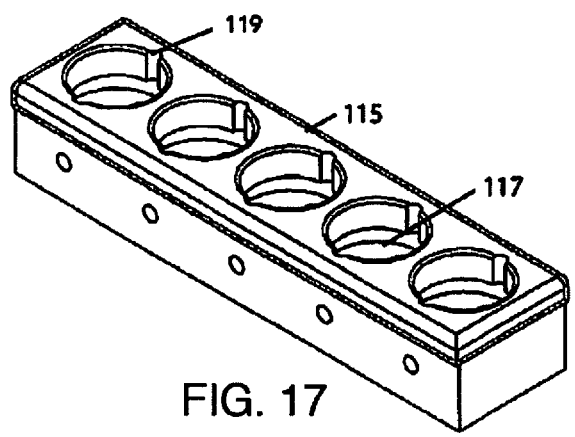
FIG. 17 illustrates an embodiment of digital aroma system components for a headset.
Figure 18:
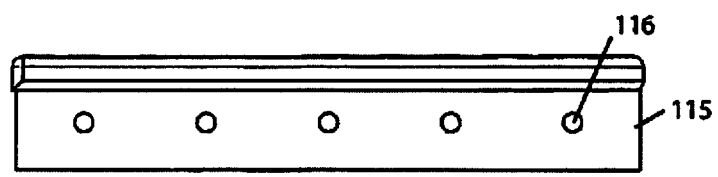
FIG. 18 illustrates a side view of a tablet computer with a digital aroma system attached to a back surface.

In an embodiment with reference to FIGS. 16-20, a fragrance cassette matrix 115 is illustrated. FIG. 16 illustrates a top view of a fragrance cassette matrix 115 and FIG. 17 illustrates a perspective top view of the cassette matrix 115. The cassette matrix 115 can have cartridge openings 117 that each holds a fragrance cartridge. FIG. 18 illustrates a side view of the cassette matrix 115. The illustrated embodiment of the cassette matrix 115 can have five cartridge openings 117 that securely hold five fragrance cartridges 101 in a single row configuration. The cartridge opening 117 in the cassette matrix 115 can each have two air channels, for example, one inlet 114 and one outlet 116. The fragrance cartridges 101 can be easily placed in and removed from the opening 117. The cartridge openings 117 can also have tab slots 119 which can be aligned with the cartridge tabs and provide a mechanism for securing the fragrance cartridges to the cartridge opening 117. For example, when the fragrance cartridge is placed in the cartridge opening 117, the cartridge tabs can be placed in the tab slots 119. Once the fragrance cartridge is fully inserted into the cartridge opening 117, the fragrance cartridge can be axially rotated within the opening 117 so that the tabs are no longer aligned with the tab slots 119. By offsetting the tabs from the tab slots 119, the fragrance cartridge can be secured within the cassette matrix 115.

Figure 19:
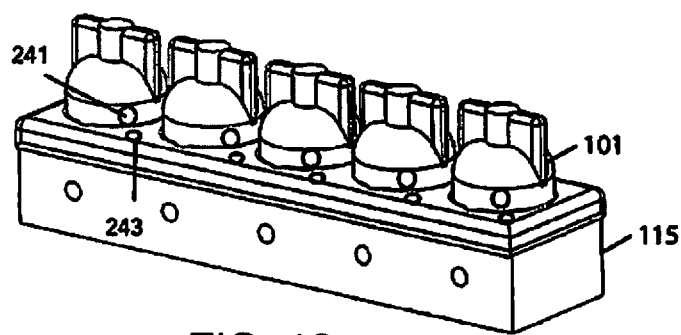
FIG. 19 illustrates a side view of a smart phone with a digital aroma system attached to a back surface.
Figure 20:
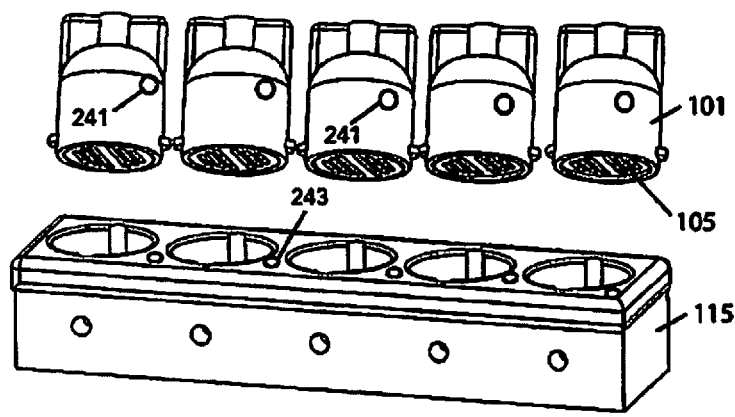
FIG. 20 illustrates a top cross section view of an embodiment of a fragrance cartridge.

FIG. 19 illustrates a perspective top view of the cassette matrix 115 with the fragrance cartridges 101 positioned in the cartridge opening 117. In the illustrated embodiment, the cartridges 101 have been inserted into the cartridge opening 117 with the tabs aligned with the tab slots and then rotated 90 degrees after being fully inserted. FIG. 20 illustrates a perspective top view of the cassette matrix 115 and with the cartridges 101 positioned over the sockets openings 117. The cartridges 101 are interchangeable within the cassette matrix 115.

Figure 21:
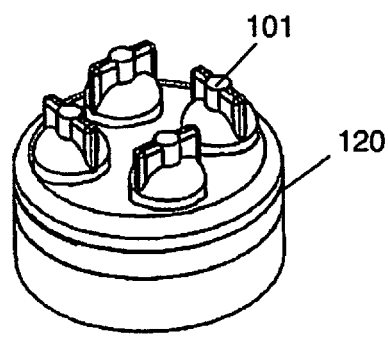
FIG. 21 illustrates a side cross section view of an embodiment of a fragrance cartridge.

As discussed, each cartridge 101 can include identification information which identifies the fragrance so that the digital aroma system can properly direct air to the target fragrance cartridge 101 regardless of its position in the cassette matrix. For example, in an embodiment, each fragrance cartridge 101 can include a radio frequency identification (RFID) tag 241 and the cassette matrix 115 can include RFID readers. The RFID tag 241 can transmit fragrance identification and a number of fragrance dispersions as well as a cartridge identification code. The RFID reader 243 can read the identification information from the RFID tag 241 on the fragrance cartridge 101 and additional cartridge information, which can be used by the system. For example, the system displays the fragrance on a system output and directs the air to the proper fragrance cartridge 101. In other embodiments, the cassette matrix can hold more fragrance cartridges 101 in different configurations such as a 2×6, 3×8 or any other one or two ore three dimensional array configuration including circular cassette matrix 120 configuration as illustrated in FIG. 21.

Figure 22:
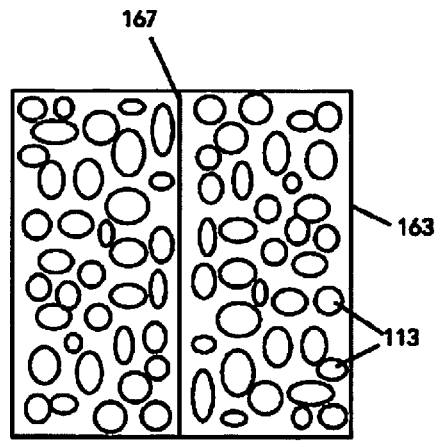
FIG. 22 illustrates a top cross section view of an embodiment of a fragrance cartridge.
Figure 23:
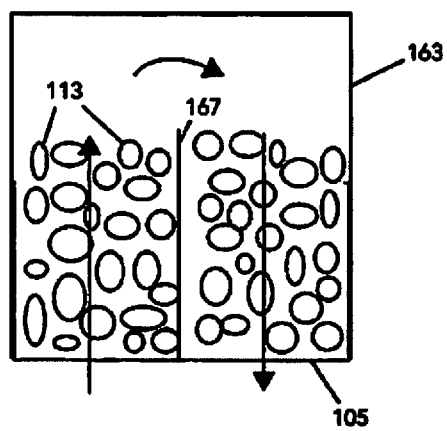
FIG. 23 illustrates a side cross section view of an embodiment of a fragrance cartridge.

In different embodiments, the fragrance cartridges used with the digital aroma system can be configured with an air inlet and a scented air outlet on the same side of the fragrance cartridge. With reference to FIG. 22, a top cross section view of a cube shaped housing 163 embodiment of a fragrance cartridge 162 is partially filled with fragrance infused substrates. The fragrance cartridge 162 includes a divider 167 that extends across a center that is the width of the housing 163. FIG. 23 illustrates a side cross section view of the cube shaped housing 163 embodiment of a fragrance cartridge 101 with a divider that is against the lower surface of the housing 163 but does not extend to the top of the housing 163. The arrows illustrate the flow path of air through air inlet holes in the bottom of the housing 163 over the divider and back through air outlet holes in the bottom of the housing 163.

Figure 24:
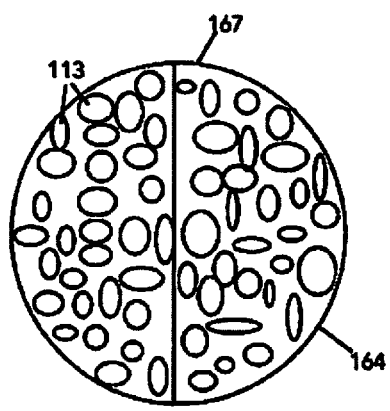
FIG. 24 illustrates a top perspective view of an embodiment of a fragrance cartridge cassette.
Figure 25:
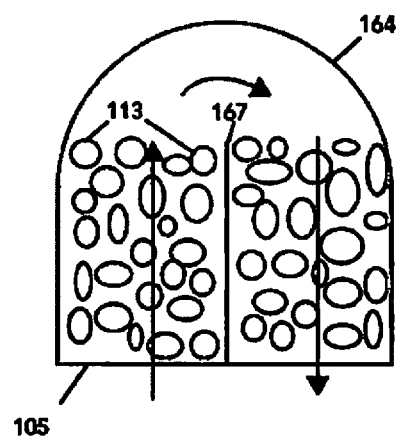
FIG. 25 illustrates a top perspective view of an embodiment of a cassette and a manifold module.

In other embodiments with reference to FIGS. 24 and 25, the fragrance cartridge 164 can have a bullet shaped housing with a lower cylindrical shaped housing and an upper half spherical shaped housing. The divider 167 is positioned against the lower surface of the housing 165 and provides a passageway above the divider 167. The arrows illustrate the flow path of air through air inlet holes in the bottom of the housing 164 that flow over the divider and back through air outlet holes in the bottom of the housing 164.

Figure 26:
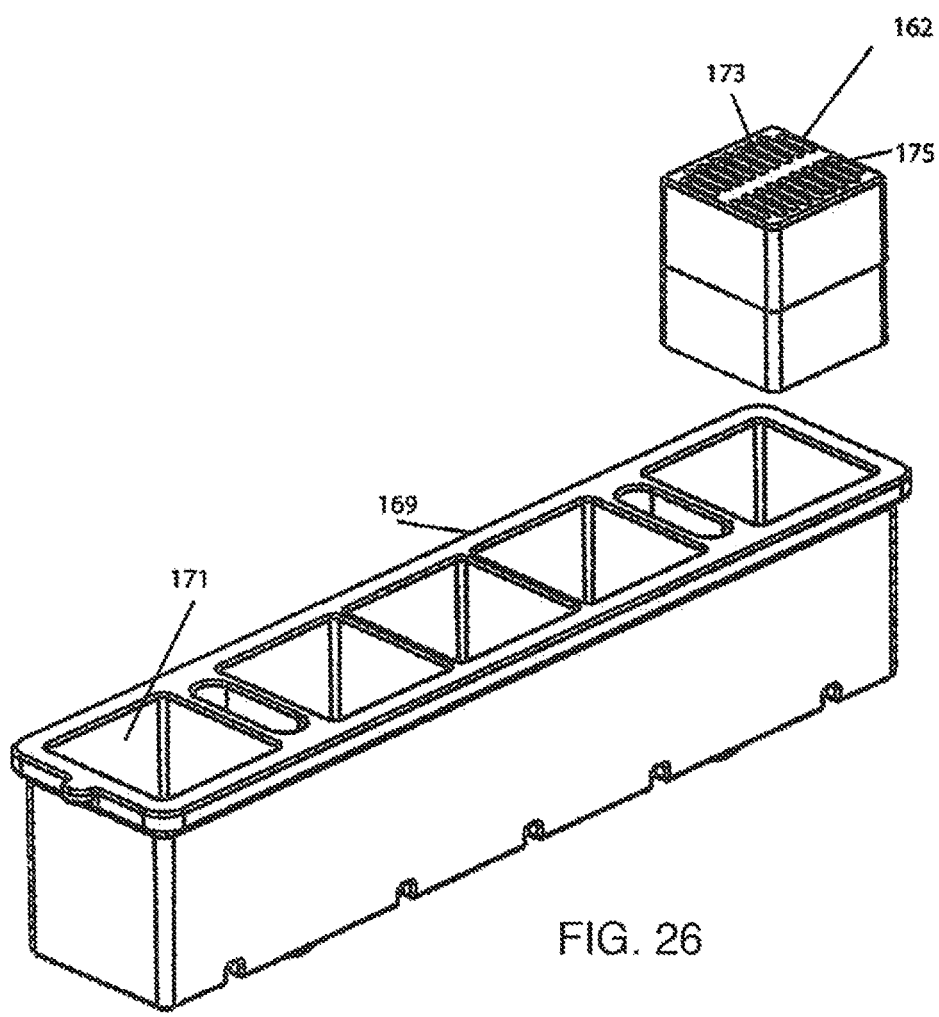
FIG. 26 illustrates a bottom perspective view of an embodiment of a cassette for holding fragrance cartridges.

Because the cartridges have air inlets and scented air outlets on the same lower surface, the cartridges can be mounted in a cassette that holds the cartridges against a manifold that has both air inlets and scented air outlet paths. FIG. 26 illustrates a bottom perspective view of an embodiment of a cassette 169 that has open bottom slots 171 that allow the individual fragrance cartridges 162. The fragrance cartridges 162 can be inserted or replaced from the cassette 169. As discussed, the air inlet 173 and the scented air outlet 175 of the fragrance cartridge 162 can be on the same planar side surface of the cartridge 162. Thus, the top of the cartridge slot 171 can be closed since air does not flow through the cassette 169.

Figure 27:
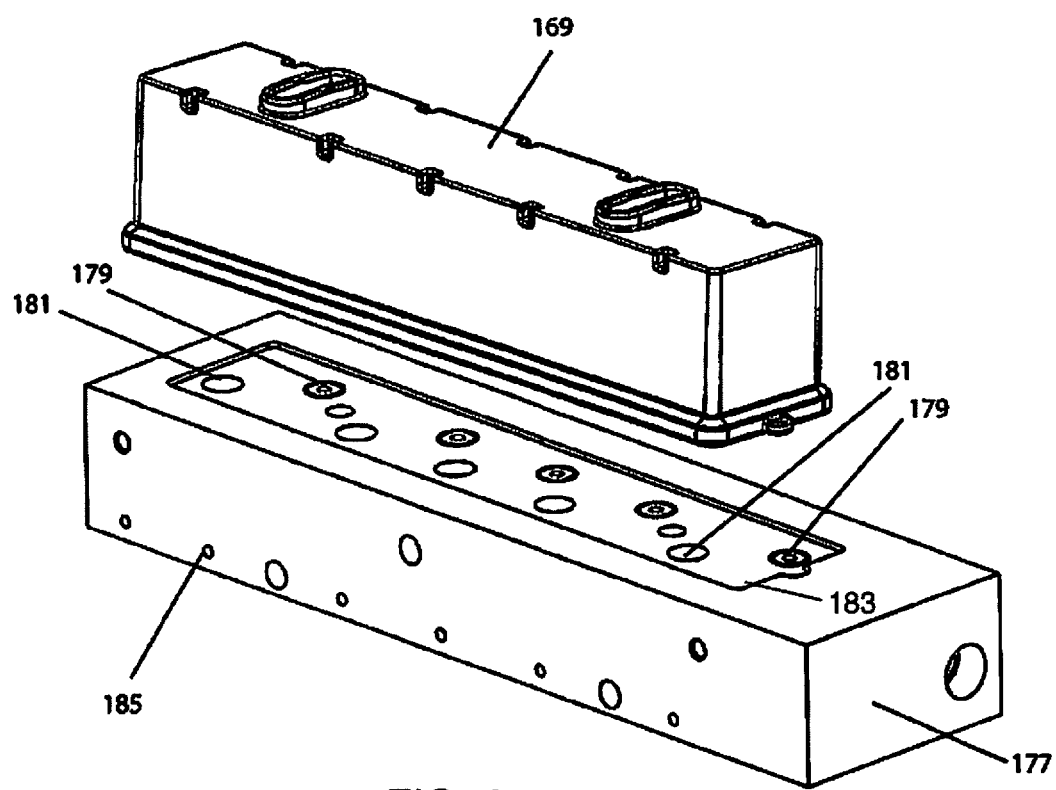
FIG. 27 illustrates an exploded perspective view of an embodiment of a cassette and a manifold module.

With reference to FIG. 27, a perspective view of an embodiment of the cassette 169 and a manifold module 177 is illustrated. The cassette 169 is in the upright position which shows the solid upper surface. The air inlet and scented air outlets of the fragrance cartridges are exposed on the lower surface of the cassette 169. The manifold module 177 can have a recess 183 that corresponds with the outer lower perimeter of the cassette 169. The manifold module 177 can also have internal air passageways that are connected to the fragrance cartridges. In this embodiment, the manifold module has a row of fresh air outlet holes 179 and a row of scented air inlet holes 181. The cassette 169 can be placed in the recess 183 and held against the manifold module 177 with a releasable coupling mechanism. A gas seal such as an air tight gasket can be placed between the fragrance cartridges and the manifold module 177 to separate the different fragrance cartridges and seal the fresh air outlet holes 179 and air inlet holes 181. The side surfaces of the manifold module 177 can have side holes 185, which can be connected to the internal passageways within the manifold modules 177 as well as the fresh air outlet holes 179 and air inlet holes 181.

Figure 28:
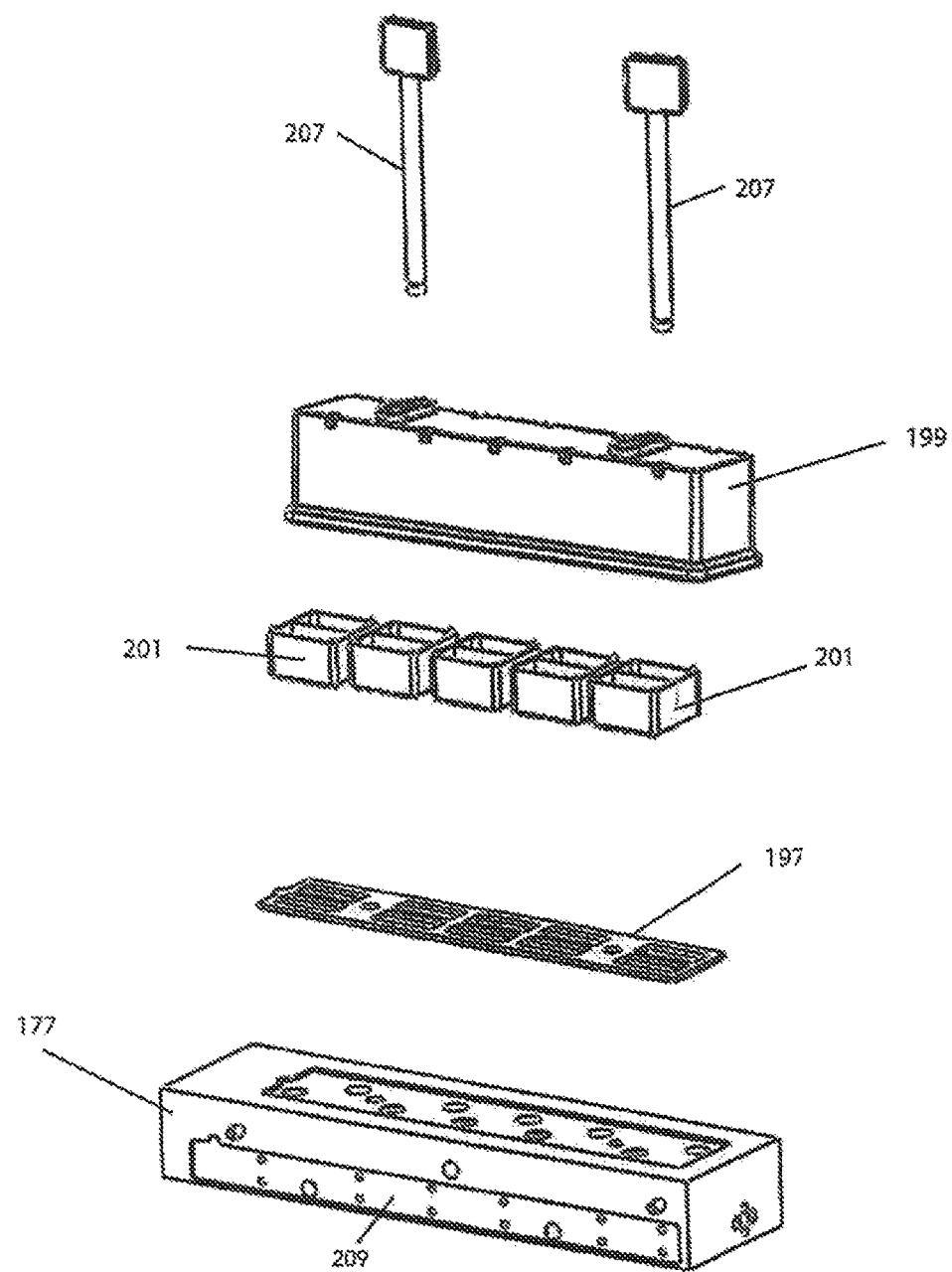
FIG. 28 illustrates an exploded view of an embodiment of a manifold module and cassette assembly.

With reference to FIG. 28, an exploded view of a different embodiment of a manifold module 177 and cassette assembly is illustrated. In this embodiment, the assembly can include a cassette chamber 199 that surrounds a plurality of different cassette bead retainers 201 which can each have a different fragrance. Different fragrance infused substrates can be placed in each of the cassette bead retainers 201 that are within the cassette chamber 199. A cassette gasket seal 197 is placed between the cassette 169 and the manifold module 177 to prevent air from flowing between the different cassette bead retainers 201 or out the top and sides of the cassette chamber 199. The cassette assembly is held to the manifold module 177 by tightening locking pins 207 that extend through the cassette assembly components. The locking pins 207 can compress the gasket 197 between the cassette chamber 199 and the manifold module 177 which creates an air tight assembly. When the adjacent manifold modules 177 are attached to each other, a manifold gasket 209 can be placed between the manifold modules 177 to create air tight seals for the aligned and coupled side air holes.

Figure 29:
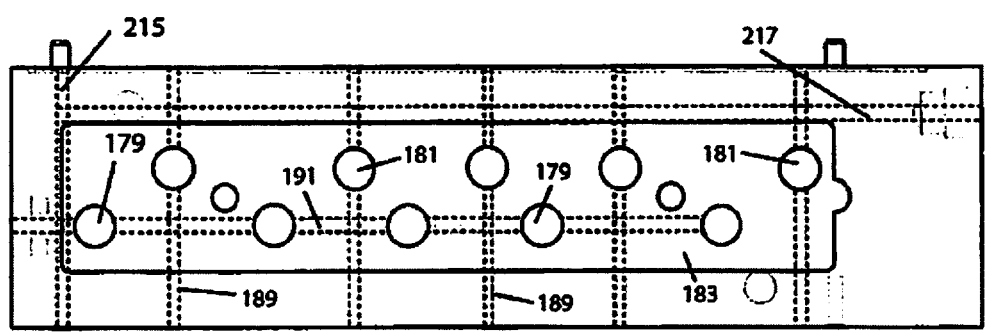
FIG. 29 illustrates a top view of an embodiment of a manifold module.

With reference to FIG. 29, a top view of an embodiment of a manifold module 177 shows the internal passageways, which include a length passageway 191 that is connected to the fresh air outlets 179 that extends along the length of the manifold module 177. The internal passageways include parallel width passageways 189 that extend across the width of the manifold module 177 where each of the width passageways 189 are coupled to a scented air inlet 181. The length passageway 191 is offset vertically from the width passageways 189 so that they are not connected. The manifold module 177 can also include an inlet air passageway 215 that extends through the width of module 177 on one edge and an outlet scent passageway 217 that extends along the length of the module 177 on another edge. When multiple modules 177 are connected, the inlet air passageways 215 can be connected to form a longer inlet air passageway that extends across the entire width of the assembly. In contrast, when multiple modules 177 are connected, the system may only use the outlet scent passageway 217 of the end module 177, leaving the outlet scent passageways 217 of the other modules 177 unused.

Figure 30:
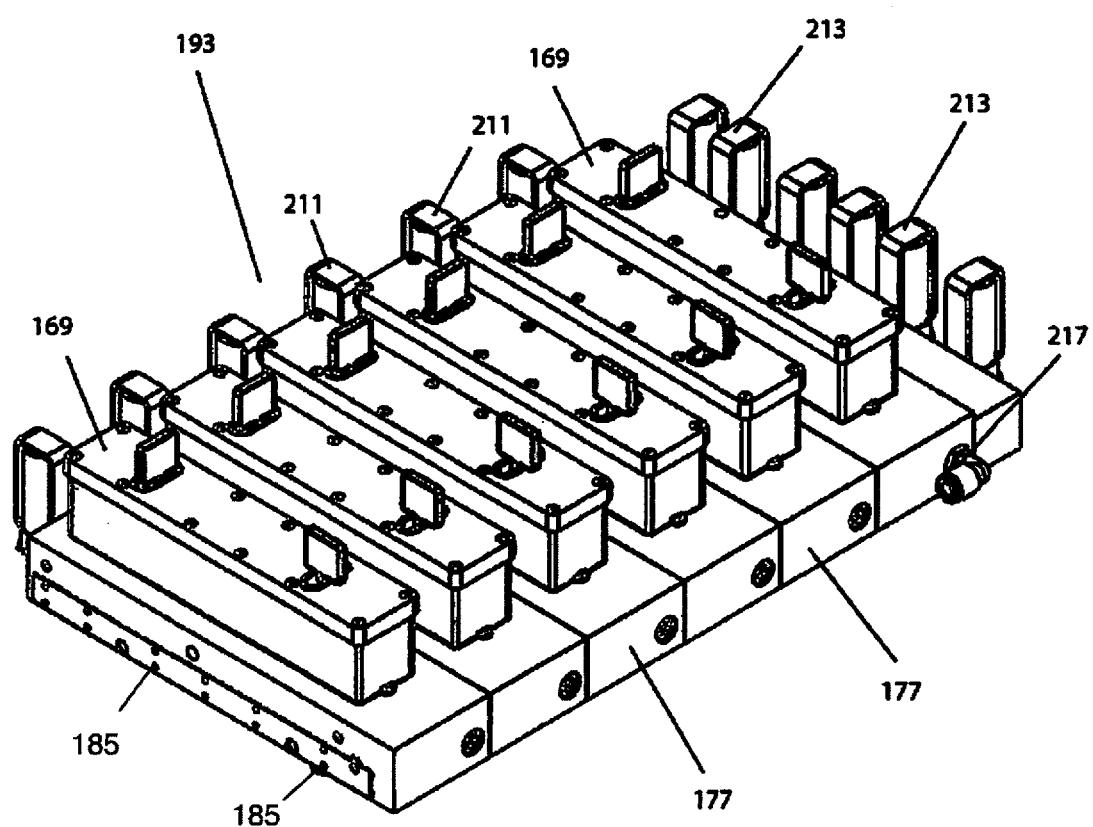
FIG. 30 illustrates a top perspective view of multiple manifold modules coupled together.

With reference to FIG. 30, multiple manifold modules 177 can be coupled together with the side air passageway holes 185 aligned to form a larger digital fragrance system. By connecting and sealing the side holes 185 to the side holes 185 of the adjacent manifold module 177, the digital fragrance system can be expanded to include any number of fragrance cartridges. In the illustrated example, there are six manifold modules 177 with each of the manifold modules 177 containing five fragrance cartridges. In this example, the illustrated digital aroma system assembly 193 can include a total of thirty fragrance cartridges. A plurality of inlet valves 211 can be coupled to the inlet air passageways on one end of each of the manifold modules 177. Likewise, a plurality of outlet valves 213 can be coupled to the outlet scent passageways on one of the end manifold modules 177 and the opposite ends of the outlet scent passageways can be sealed to prevent air from escaping. Air can be directed through the digital fragrance system to any individual fragrance cartridge by controlling the open/closed positions of the inlet valves 211 and the outlet valves 213.

Figure 31:
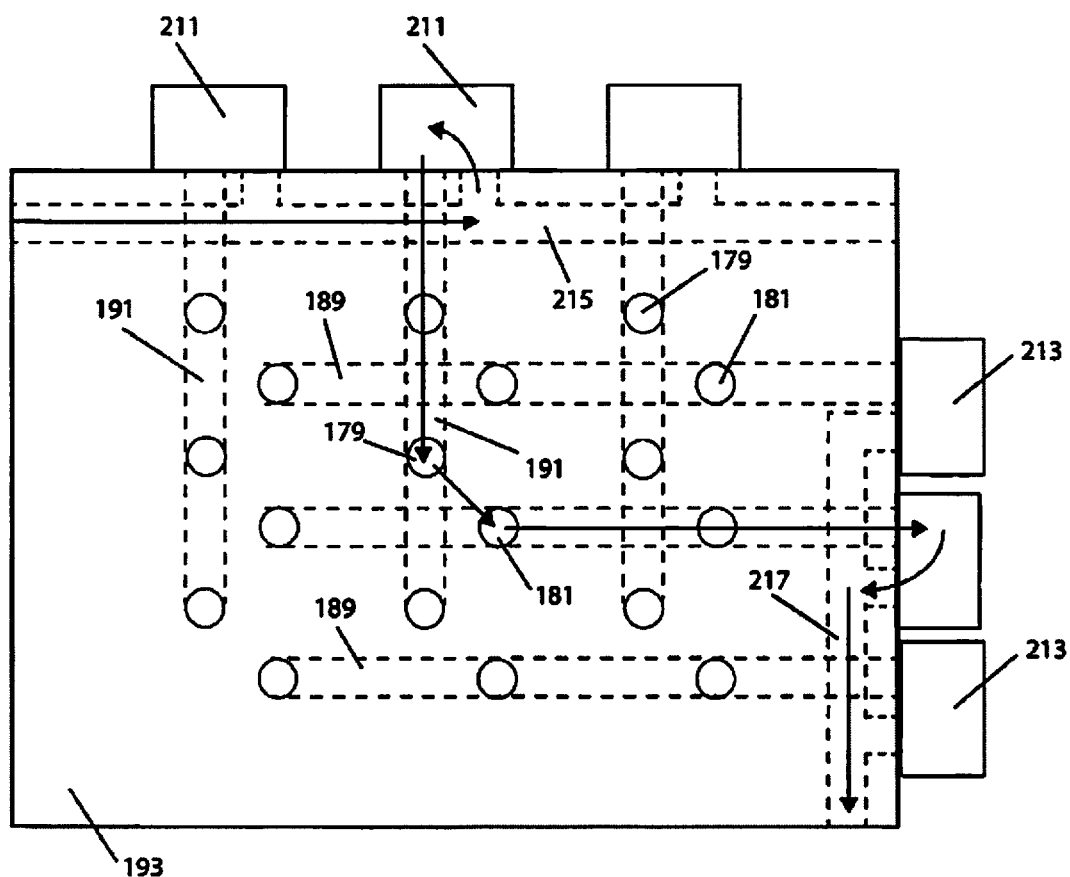
FIG. 31 illustrates a top view of an embodiment of a digital aroma system with a matrix of internal passageways.

With reference to FIG. 31, the illustrated digital aroma system 193 is formed from a plurality of manifold modules that can have an array of internal passageways 161 which can be coupled to inlet valves 211 and outlet valves 213 which are opened and closed to control the scented air outlet path. By actuating (opening) one inlet valve 211 and one outlet valve 213 and keeping all other inlet valves 211 and outlet valves 213 closed, a passageway to a specific fragrance cartridge can be selected by the digital aroma system.

In an embodiment with reference to FIG. 31, pressurized air from a fan or pump can be applied to the inlet air passageway 215. When one of the inlet valves 211 is actuated, pressurized air can flow through the corresponding length passageway on a selected row of fragrance cartridges in a single cassette. When one of the outlet valves 213 is open, air can flow through the fragrance cartridges and scented air can flow to the outlet passageway 217. From the simplified digital aroma system 193, the scented air can be directed towards the nose of the system user. In an alternative embodiment, a vacuum or low pressure from a fan or pump can be applied to the outlet scent passageway 217. When one of the inlet valves 211 is opened, air can pulled through the corresponding length passageway on a manifold module 177. Air can then flow through one of the fragrance cartridges to the outlet passageway 217 through the fan or pump and be directed towards the nose of the system user. The valves can be actuated by a valve controller(s) that is controlled by a system processor in response to a scent release signal. Each individual fragrance stored in the digital aroma system 193 can be output by actuating a combination of one inlet valve and one outlet valve. In some embodiments, it can be desirable to mix a plurality of fragrances which can be performed by opening valves to a plurality of fragrance cartridges.

Figure 32:
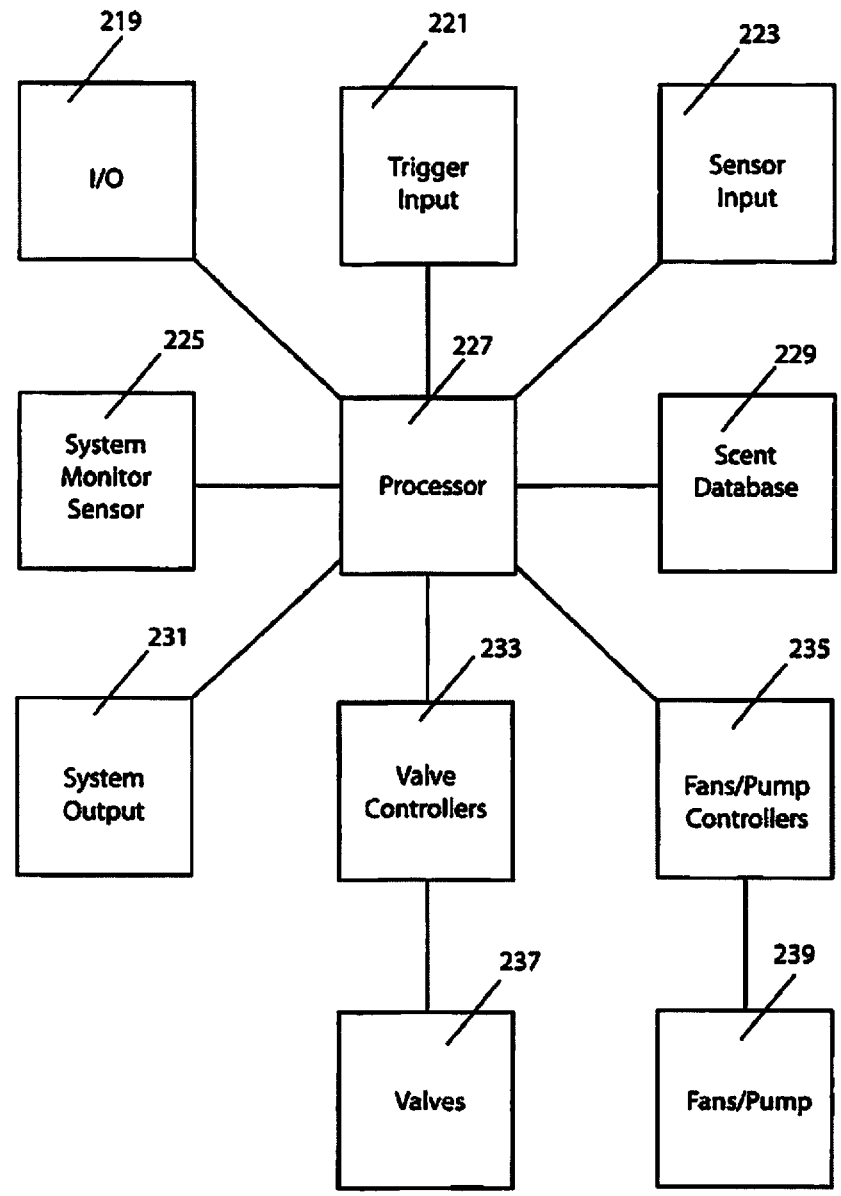
FIG. 32 illustrates a block diagram of the components within an embodiment of a digital aroma device.

FIG. 32 illustrates a block diagram of possible components of a digital aroma system which can include: an I/O 219, a display 255, a sensor input 223, system monitor sensors 225, processor 227, a scent database 229, a system monitor sensor 225, a system output 231, valve controllers 233, vales 237, fan/pump controllers 235 and fans/pumps 239. The I/O 219 can be a transceiver that allows communications between the digital aroma system and other media devices, servers, smartphones, servers, other digital aroma systems and other computing devices. In an embodiment, the I/O 219 can provide system communications wirelessly through Blue Tooth, Wi-Fi, RFID or similar technologies with other devices which can provide control signals for releasing fragrances. The display 255 can be a visual display such as an LCD or LED alphanumeric output display.

When the digital aroma system is used, it can go through a startup procedure which identifies each fragrance cartridge stored in the system. As discussed, the fragrance cartridges can have an identification system, which are read by the system monitor sensors 225. For example, in an embodiment, each of the plurality of fragrance cartridges includes an RFID tag that identifies a scent of the dry fragrance cartridge and an RFID reader reads the RFID tags of the fragrance cartridges. The RFID readers can be system monitor sensors 225. The digital aroma system includes a visual display 255 which can display the scent of the dry fragrance cartridge that has been emitted.

In an embodiment, the digital aroma system can include software running on a local processor that can communicate through the I/O 219 to the Internet via a cloud service. This communication capability can be used with the system monitor sensor 225 for remote monitoring of the cassettes and fragrance cartridges, the duration of the number of uses, and it remotely monitors the health of the pump and/or fan and the health of the digital aroma system to ensure the system components are working properly. If errors are detected in any of the system components, the processor 227 of the digital aroma system sends alerts to a user or system administrator who can identify the error(s) through error signals transmitted to the system output 231 when something is not working properly. The system output 231 can be a visual display, an audio output device and/or a digital wireless communication output.

In an embodiment the digital aroma system can include an audio recognition system that can interpret sound command signals, such as vocal commands. The I/O 219 can include a microphone, which can detect audio signals and the processor 227 can run audio signal recognition software. The system may require the user to state an initial recognition word followed by a command. For example, the recognition word may be "Inhalio" and the command can be include the fragrance word. Thus, a user can say "Inhalio disperse lavender." This audio signal can be received by the microphone I/O 219 and interpreted by the processor 227 as the recognition word followed by the disperse lavender command. The processor 227 can then control the valve controllers 233 and/or fan/pump controllers 235 to direct air through the lavender fragrance cartridge so the aroma device emits the lavender fragrance. In other embodiments, other types of audio signals can be interpreted by the system such as claps or whistles and result in the emission of fragrances that are programmed to correspond to the audio signals.

Figure 33:
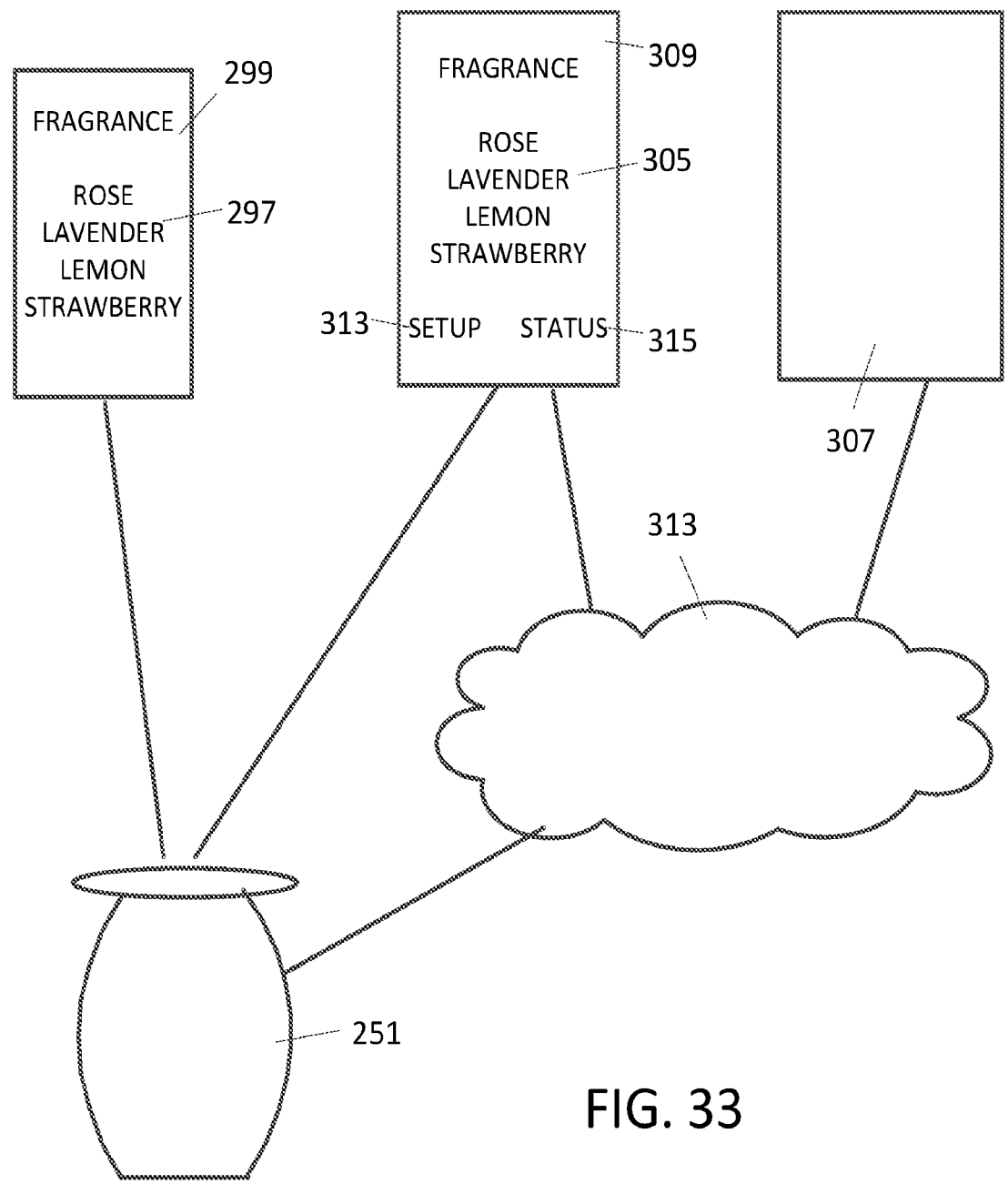
FIG. 33 illustrates a block diagram of an embodiment of a digital aroma system.

With reference to FIG. 33, a diagram showing the network communications between a computing device 309, a server 307 and an aroma device 251 is illustrated. The aroma device 251 can be part of the "internet of things" and function as an internet connected intelligent device that can communicate with other connected devices 308. As discussed, the aroma device 251 can be interacted with a network 313 such as the internet with a network connected to a computing device(s) 309 such as a smartphone, a tablet, or a computer.

In different embodiments the digital aroma system can communicate with other internet connected devices 308 to provide coordinated or reactive operations. Possible connected devices can include: lights, lamps, appliances, furniture, music systems, media players, televisions, etc. For example, the digital aroma system 251 may be connected to other home network connected devices 308, such as a light bulb that changes the ambient light color and light output and/or an audio system that can emit music that is complimentary to the aroma that is selected and dispersed. A user may want a relaxing environment and provide a fragrance signal for a relaxing chamomile aroma to the aroma system 251. The aroma system 251 may transmit the relaxing chamomile fragrance output through the network 313 to the ambient lighting and audio systems (connected devices 308), which can respond by providing complimentary outputs. The lighting can dim and change to a warm glow and the audio system can output soft ambient music such as low volume classical instrumental songs. By coordinating the operations of these different connected devices 308, the user's operation of these connected devices 308 is greatly simplified.

In other embodiments with reference to FIG. 32, the digital aroma system can respond to input signals from other devices. For example, the digital aroma can receive signals from a media player. The I/O 219 of the digital aroma system can couple to a media player that can detect audio or fragrance signals for playback in an audio or video media before the corresponding audio or video are output by the media player to the user. For example, a video media being played may include fireworks and the distinctive sounds of the firework explosions. The audio trigger recognition software running on the processor 227 may identify the fireworks sound and associate this sound with the fragrance of burning sulfur. In an embodiment, the audio recognition system may detect the fragrance associated audio signal through the scent database 229 and the audio recognition software on the processor 227 may actuate the delivery of the fragrance by actuating the correct set of valves 237 before the audio trigger is output through the speaker by the known time delay period so that the fragrance is delivered to the viewer at the moment when the audio trigger sound is being heard. In other embodiments, the aroma system can be configured to output specific fragrances in response to specific types of events in a story being output by television and/or a movie.

In some embodiments, the aroma device 251 can be controlled by a remote control 299 that can have dedicated buttons 297 for a plurality of fragrances. When a user presses a desired fragrance button 297, the remote control 299 can transmit a wireless fragrance signal directly to the aroma device 251 that can then receive the wireless fragrance signal and respond by emitting the selected aroma. Various control signal transmission paths can be used between the computing device 309 and the aroma device 251. For example the RF signal can be a short range signal such as a Bluetooth signal or a Wi-Fi signal that is transmitted directly from the computing device 309 to the aroma device 251. In another embodiment, the RF signal can be a Wi-Fi signal that is transmitted from the computing device 309 to a network receiver, which then transmits the signal to the aroma device 251. The aroma device 251 can respond by emitting the user selected fragrance. In this network embodiment, the user could transmit a fragrance signal from a remote location which can be transmitted through the Internet to the aroma device 251. Thus, the computing device 309 does not need to be in the same location as the aroma device 251.

In an embodiment, the computing device 309 may download and run an application program (app) that includes a user interface that can allow a user to select a desired fragrance. The app can provide a user interface to the computing device 309 that can include manually and/or automatic controls for the aroma device 251. For example, in a manual mode, the user can press a desired fragrance user interface button 305 on a user interface and the app can cause the computing device 309 to output an RF fragrance signal that can be transmitted to the aroma device. The user interface can also include various other controls. For example, if the user wishes to configure the aroma device, the user interface may press a setup button 313 or if the user wishes to see the status of the aroma device, the user can press a status button 315.

Figure 34:
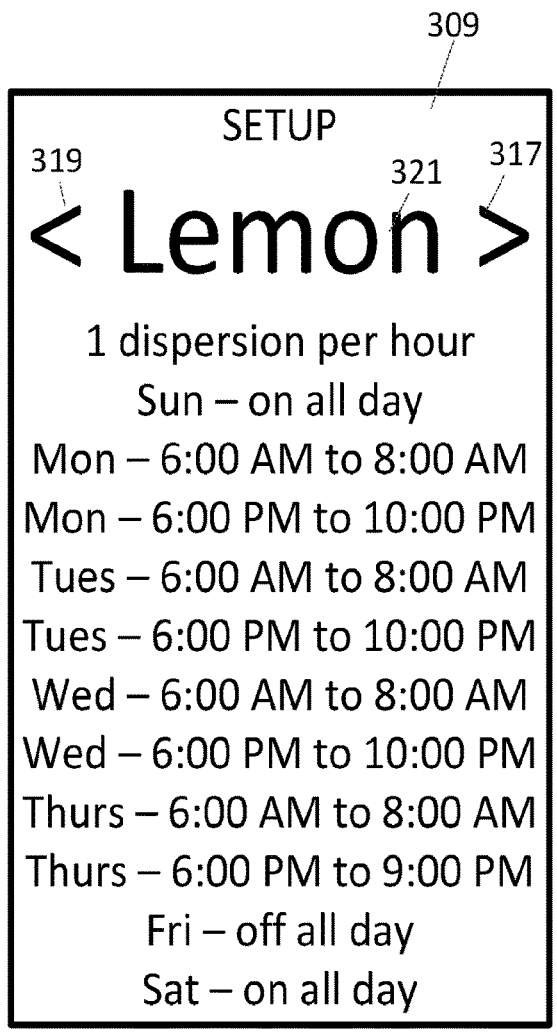
FIG. 34 illustrates an embodiment of a setup user interface on a computing device.
Figure 35:
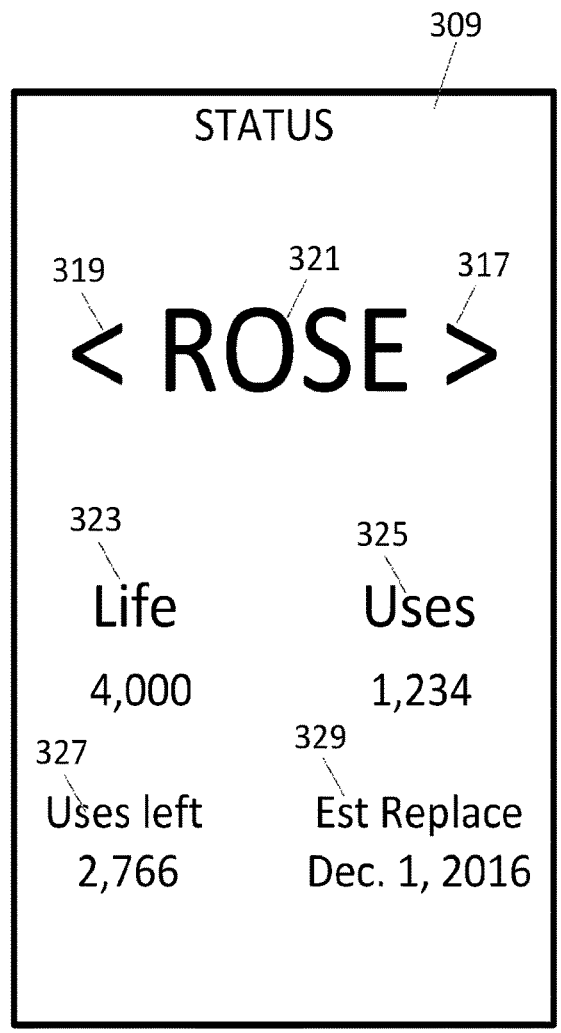
FIG. 35 illustrates an embodiment of a status user interface on a computing device.

With reference to FIG. 34, when the setup button is pressed, the user interface can display a setup page on the computing device 309 which can allow a user to program the fragrance output for each of the fragrance cartridges stored in the aroma device. In this example, the fragrance identification 321 is "Lemon" and the lemon program page is illustrated. The user can scroll between the different fragrances by pressing the forward button 317 or the backward button 319. Repeatedly touching the forward button 317 can cause the user interface to sequentially display programs for: Strawberry, Rose, Lavender and then back to Lemon. In this example, the app is currently programmed to emit one dispersion of lemon scent each hour. The dispersions can be configured at specific times each day. In the example, the system is configured to emit the lemon fragrance "Monday through Thursday" in the morning, starting at "6 AM to 8 AM," and then in the evening from "6 PM to 10 PM." On Saturday the system is configured to emit the lemon fragrance all day from "6 AM to 10 PM." On Fridays the aroma unit is not configured to emit the lemon fragrance. If the user wishes to change any of these programed controls, the user can touch the settings and make any desired adjustments. When touched, the program setting can be adjusted as desired.

When the user touches the status button, the user interface of the app on the computing device 309 can display the status of the fragrance cartridge. As discussed, the fragrance cartridge can include information in an RFID tag that can be read by the aroma device. In the example, the information can identify the fragrance cartridge as "Rose" with a life of 4,000 dispersions. With reference to FIG. 36, the fragrance identification 321 is "Rose." The user interface displays the life 323 as 4,000 dispersions. As the fragrance cartridge is used, the aroma device keeps track of these dispersions and the use information 325 can be displayed. In this example, the rose fragrance cartridge has been used 1,234 times. The aroma device processor can calculate and display the number of dispersions left 327. The aroma device processor can also predict the estimated replacement date 329 based upon past use. In this example, the processor may calculate that the user actuates an average of 10 dispersions per day of the rose fragrance. With 2,766 dispersions left, the processor can estimate that there are 276.6 days of dispersions left in the rose fragrance cartridge and calculating forward from this date, the processor can determine that the estimated replacement date 329 is "Dec. 1, 2016." When a fragrance cartridge is near depletion, the app can inform the user that the fragrance cartridge now needs to be replaced and when the fragrance cartridge is depleted, the app can inform the user that the fragrance cartridge must be replaced. In an embodiment, the app can have an integrated fragrance cartridge purchasing option.

While the digital aroma system has been shown in many of the figures as having a vase shaped housing. A vase is just one example of a possible housing shape. In other embodiments the digital aroma system can be integrated into another housing having a different shape. Examples of other housing shapes can include any geometric shape that can accommodate the fragrance cartridge(s), fans/pumps, air inlet and fragrance outlet. In other embodiments, the aroma system can be integrated into different devices that can perform different functions. Examples of different devices can include: automobiles, home appliances, furniture lamps, headboards, tables, chairs, air conditions, heaters, fans, etc. The described digital aroma system can be integrated into the heating, ventilation and air conditioning (HVAC) systems of vehicles such as cars, planes, trains, boats, etc. The HVAC controls of these vehicles can include fragrance output controls so that when a user presses a fragrance button, the aroma system can disperse the selected fragrance through the HVAC vents to the passenger area of the vehicles. The aroma system can also be integrated into or used with other HVAC devices such as air conditions, heaters, and fans. In other embodiments, the aroma system can be integrated into furniture that a person can sit or sleep in or near such as chairs, beds and lamps.

The present invention addresses several issues that are currently found in fragrance systems. Some fragrance systems have tried to use scented oils, which are cumbersome and messy. In contrast, this inventive digital aroma system uses fragrance cartridges, which have dry beaded and sealed units coupled to a cassette and manifold, which provides a self-contained system. The fragrance is mixed with the air from dry particles, which are infused into substrates such as beads that remain enclosed in individual chambers in order to seal the aroma for freshness until the fragrance cartridge is installed in the digital aroma system and delivered through the scent outlet to the user. Because of the dry nature of the fragrance materials there is no lingering aroma effect and no volatile organic compounds (VOCs).

In the present digital aroma system invention, the user can easily change the fragrance cartridges and may only need to replace the cartridges every few months depending upon the scent use. In an embodiment, the digital aroma system can monitor the number of times each of the fragrance cartridges is used. When the life of the cartridge is reaching its end, the system can warn the user that the cartridge needs to be replaced. Thus, the cartridges are only replaced as needed. The longevity of each dry fragrance infused beaded cartridge is anywhere from 1,000-4,500 dispersions. In other embodiments, fragrance cartridges with larger chambers hold more fragrance infused substrate materials that can last longer with more dispersions.

The present digital aroma system invention addresses the issue of the replacement of fragrance cartridges by the consumer. The digital aroma system allows the ease of swapping out several fragrances simultaneously by removing and replacing a single cassette of the digital aroma system. The cassette can contain six or more individual fragrance cartridges containing dry fragrance infused substrate materials. In other embodiments, the cassette is not limited to six fragrance cartridges. For example, the cassette can hold a single fragrance cartridge and in other embodiments the cassette can have couplings to hold ten to twenty or more fragrance cartridges in a cassette system. In addition, the consumer can also change each individual aroma cartridge within the cassette system by simply exchanging each aroma cartridge within the cassette or replacing the entire cassette.

The digital aroma system can include a cassette having a manifold, which holds a plurality of fragrance cartridges. The manifold has air inlets and scent outlets that are coupled to the fragrance cartridges which can have hollow housings which are filled with dry fragrance infused particles such as balls or other loose objects. The cartridge housings can have couplings such as threads or tabs, which can provide a gas tight connection between the cartridges and the manifold. The couplings also allow users to replace or change the fragrance cartridges. The cartridges can also have identification mechanisms, which provide an identification signal output such as a radio frequency identification tag. The identification signal output can identify the fragrance in the cartridge and control the number of fragrance outputs that the cartridge can provide. The digital aroma system can have readers, which can read the identities of the fragrance in the cartridges and store this fragrance and cartridge location information so that a desired fragrance can be controlled and emitted by the digital aroma system.

For the sake of clarity, the processes and methods herein have been illustrated with a specific flow, but it should be understood that other sequences may be possible and that some may be performed in parallel, without departing from the spirit of the invention. Additionally, steps may be subdivided or combined. As disclosed herein, software written in accordance with the present invention may be stored in some form of computer-readable medium, such as memory or CD-ROM, or transmitted over a network, and executed by a processor.

All references cited herein are intended to be incorporated by reference. Although the present invention has been described above in terms of specific embodiments, it is anticipated that alterations and modifications to this invention will no doubt become apparent to those skilled in the art and may be practiced within the scope and equivalents of the appended claims. More than one computer may be used, such as by using multiple computers in a parallel or load-sharing arrangement or distributing tasks across multiple computers such that, as a whole, they perform the functions of the components identified herein; i.e. they take the place of a single computer. Various functions described above may be performed by a single process or groups of processes, on a single computer or distributed over several computers. Processes may invoke other processes to handle certain tasks. A single storage device may be used, or several may be used to take the place of a single storage device. The present embodiments are to be considered as illustrative and not restrictive, and the invention is not to be limited to the details given herein. It is therefore intended that the disclosure and following claims be interpreted as covering all such alterations and modifications as fall within the true spirit and scope of the invention.

What is claimed is:

1. A digital aroma apparatus comprising:
    a plurality of fragrance cartridges, each of the fragrance cartridges comprising:
        a cartridge housing having an inlet and an outlet; and
        a plurality of dry fragrance infused substrates within the cartridge housing;
    a housing for holding the plurality of fragrance cartridges, the housing having air passages wherein each of the air passageways is connected to one of the fragrance cartridges and each of the plurality of fragrance cartridges are individually removable from the housing;
    a plurality of pumps or fans for directing air through the inlet and the outlet of the fragrance cartridges; and
    a receiver for receiving digital aroma signals coupled to a processor that selectively controls the plurality of pumps or fans.

2. The digital aroma apparatus of claim 1, wherein the dry fragrance infused substrates are beads or substrate materials infused with a plurality of different fragrances.

3. The digital aroma apparatus of claim 1, wherein each of the plurality of fragrance cartridges includes a coupling mechanism for securing the cartridge housing to the housing of the digital aroma apparatus.

4. The digital aroma apparatus of claim 1, wherein each of the plurality of fragrance cartridges includes a radio frequency identification (RFID) tag that identifies a scent of the dry fragrance cartridge and the processor is coupled to an RFID reader which reads the RFID tags of the fragrance cartridges.

5. The digital aroma apparatus of claim 1, wherein the digital aroma apparatus includes a visual display for displaying the scent of the dry fragrance cartridge that is being emitted by the digital aroma apparatus.

6. The digital aroma apparatus of claim 1, further comprising:
    a remote control having a wireless transmitter which transmits the digital aroma signals to the receiver.

7. The digital aroma apparatus of claim 1, further comprising:
    a computing device running a fragrance control app, the computing device having a wireless transmitter which transmits the digital aroma signals to the receiver.

8. The digital aroma apparatus of claim 7, wherein computing device running the fragrance control app includes a future schedule for emission of the dry fragrances from the plurality of fragrance cartridges.

9. The digital aroma apparatus of claim 1, further comprising:

a server which receives the digital aroma signals from the computing device and stores the digital aroma signals in a server database.

10. The digital aroma apparatus of claim 1, further comprising:
a plurality of pressure sensors coupled to the processor within the housing of the digital aroma apparatus, wherein when air flows through the fragrance cartridges a pressure differential across the fragrance cartridges is measured by the pressure sensors and the processor emits a fan error signal when the pressure differential across is below a predetermined expected pressure differential range.

11. The digital aroma system of claim 1, wherein the fragrance cartridges each have gratings at the inlet and the outlet that keeps the solid fragrance material within the cartridge housings.

12. A digital aroma system comprising:
a plurality of fragrance cartridges, each of the fragrance cartridges comprising:
a cartridge housing having an inlet and an outlet; and
a plurality of dry fragrance infused substrates within the cartridge housing;
a manifold coupled to a cassette that removably holds the plurality of fragrance cartridges;
a plurality of pumps or fans for directing air through the inlet and the outlet of the fragrance cartridges;
a receiver for receiving a digital aroma signal coupled to a processor that selectively controls the plurality of pumps or fans; and
a housing wherein the manifold, the plurality of pumps or fans, and the receiver are within the housing.

13. The digital aroma system of claim 12, further comprising:
a second manifold coupled to a second cassette that removably holds a second plurality of fragrance cartridges, wherein the second manifold is coupled to the manifold.

14. The digital aroma system of claim 12, wherein the fan or the pump pulls the air through the manifold to cause the dry fragrances from the plurality of fragrance cartridges to flow through the scent outlet.

15. The digital aroma system of claim 12, further comprising:
a plurality of control valves, wherein the processor controls the opening and closing of the plurality of control valves to cause air flow through the manifold, the cassette and one of the fragrance cartridges associated with the digital aroma signal to provide a user selected fragrance output.

16. The digital aroma system of claim 12, further comprising:
a computing device running a fragrance control app, the computing device having a wireless transmitter which transmits the digital aroma signals to the receiver; and
programmable software running on the computing device to control the flow of air through the manifold, the cassette and the fragrance cartridge to provide a selected fragrance.

17. The digital aroma system of claim 16, wherein computing device running the fragrance control app includes a future schedule for emission of the dry fragrances from the plurality of fragrance cartridges.

18. The digital aroma apparatus of claim 12, further comprising:
a server which receives the digital aroma signals from the computing device and stores the digital aroma signals in a server database.

19. The digital aroma apparatus of claim 12, further comprising:
a transmitter coupled to the processor which transmits the digital aroma signal to an audio output device that emits an audio output that is complimentary to the digital aroma signal.

20. The digital aroma apparatus of claim 12, further comprising:
a transmitter coupled to the processor which transmits the digital aroma signal to a visual output device that emits a visual output that is complimentary to the digital aroma signal.

21. The digital aroma apparatus of claim 12, wherein the receiver is coupled to the output of a media player and the digital aroma system actuates one of the plurality of pumps or fans to direct air through the inlet and the outlet of the fragrance cartridges in response to a signal from the media player.

22. The digital aroma apparatus of claim 12, further comprising:
a microphone coupled to the processor for receiving a voice control signal wherein the digital aroma system actuates one of the plurality of pumps or fans to direct air through the inlet and the outlet of the fragrance cartridges in response to the voice control signal.

* * * * *